(12) United States Patent
Thompson et al.

(10) Patent No.: US 11,744,150 B2
(45) Date of Patent: Aug. 29, 2023

(54) SYNTHESIS OF AZA-ACENES AS NOVEL N-TYPE MATERIALS FOR ORGANIC ELECTRONICS

(71) Applicant: University of Southern California, Los Angeles, CA (US)

(72) Inventors: Mark E. Thompson, Anaheim, CA (US); Jonathan R. Sommer, Los Angeles, CA (US); Andrew Bartynski, Los Angeles, CA (US)

(73) Assignee: University of Southern California, Los Angeles, CA (US)

( * ) Notice: Subject to any disclaimer, the term of this patent is extended or adjusted under 35 U.S.C. 154(b) by 0 days.

(21) Appl. No.: 17/074,890

(22) Filed: Oct. 20, 2020

(65) Prior Publication Data

US 2021/0313517 A1    Oct. 7, 2021

Related U.S. Application Data

(63) Continuation of application No. 13/746,732, filed on Jan. 22, 2013, now abandoned.

(60) Provisional application No. 61/588,808, filed on Jan. 20, 2012.

(51) Int. Cl.
| | |
|---|---|
| *H01L 51/00* | (2006.01) |
| *C07D 471/22* | (2006.01) |
| *C07D 471/14* | (2006.01) |
| *C09K 11/06* | (2006.01) |
| *C07D 471/04* | (2006.01) |
| *H01L 51/42* | (2006.01) |

(52) U.S. Cl.
CPC ........ *H01L 51/0064* (2013.01); *C07D 471/04* (2013.01); *C07D 471/14* (2013.01); *C07D 471/22* (2013.01); *C09K 11/06* (2013.01); *H01L 51/0072* (2013.01); *C09K 2211/1044* (2013.01); *H01L 51/0078* (2013.01); *H01L 51/4246* (2013.01)

(58) Field of Classification Search
None
See application file for complete search history.

(56) References Cited

FOREIGN PATENT DOCUMENTS

| JP | 2002124384 A | * | 4/2002 | |
|---|---|---|---|---|
| WO | WO-2011140100 A2 | * | 11/2011 | ........... H01L 51/001 |

OTHER PUBLICATIONS

Isoda "Synthesis and Characterization of Electron-accepting Nonsubstituted Tetraazaacene Derivatives" Chem. Lett. 2012, 41, 937-939.*
Gawrys "Novel, Low-Cost, Highly Soluble n-Type Semiconductors: Tetraazaanthracene Tetraesters" Organic Letters 2011, vol. 13, No. 22 6090-6093.*

* cited by examiner

*Primary Examiner* — David K O'Dell
(74) *Attorney, Agent, or Firm* — Finnegan, Henderson, Farabow, Garrett & Dunner, LLP

(57) ABSTRACT

Acenes, such as aza-acenes are attractive materials for organic semiconductors, specifically for n-type materials. There are disclosed new derivatives of acenes that are fabricated using novel synthesis. For example, the disclosed fabrication strategies have allowed for the first time new aza-tetracene and aza-pentacene derivatives. The HOMO and LUMO energy levels of these materials are tunable through appropriate substitution and as predicted, deepened. There are also disclosed organic photosensitive devices comprising at least one aza-acene such as aza-tetracene and aza-pentacene.

3 Claims, 9 Drawing Sheets

| Cpd. | | $E_g$ (eV) | LUMO (eV) |
|---|---|---|---|
| aa | R=H | 2.58 | 2.24 |
| bb | R=Ph | 2.53 | 2.27 |

| | | | |
|---|---|---|---|
| cc | $R_1$=Ph $R_2$=H | 2.50 | 2.67 |
| dd | $R_1$=Ph $R_2$=Ph | 2.39 | 2.88 |
| ee | $R_1$=Cl $R_2$=H | 2.56 | 3.28 |
| ff | $R_1$=Cl $R_2$=Ph | 2.37 | 3.30 |
| gg | $R_1$=CN $R_2$=Ph | 2.13 | 3.83 |
| hh | $R_1$=CN $R_2$=H | 2.41 | 3.85 |
| $C_{60}$ film | | 2.75 | 3.7 |

OPV performance of aza-tetracene device.   ITO/subPC/*gg*/BCP//Al.

SYNTHESIS OF AZA-ACENES AS NOVEL N-TYPE MATERIALS FOR ORGANIC ELECTRONICS

CROSS-REFERENCE TO RELATED APPLICATIONS

This application claims priority to U.S. Provisional Application No. 61/588,808 filed on Jan. 20, 2012, which is incorporated herein by reference in its entirety.

STATEMENT REGARDING FEDERALLY SPONSORED RESEARCH

The subject matter of this application was prepared with U.S. Government support under Contract No. DE-SC0001013 awarded by U.S. Department of Energy. The government has certain rights in the subject matter of this application.

JOINT RESEARCH AGREEMENT

The subject matter of this application was made by, on behalf of, and/or in connection with one or more of the following parties to a joint university-corporation research agreement: University of Southern California and Global Photonic Energy Corporation. The agreement was in effect on and before the date the subject matter of this application was made, and such was made as a result of activities undertaken within the scope of the agreement.

The present disclosure generally relates to novel methods of synthesizing aza-acenes, which may be used as novel n-type materials in organic electronics.

Optoelectronic devices rely on the optical and electronic properties of materials to either produce or detect electromagnetic radiation electronically or to generate electricity from ambient electromagnetic radiation.

Photosensitive optoelectronic devices convert electromagnetic radiation into electricity. Solar cells, also called photovoltaic (PV) devices, are a type of photosensitive optoelectronic device that is specifically used to generate electrical power. PV devices, which may generate electrical energy from light sources other than sunlight, can be used to drive power consuming loads to provide, for example, lighting, heating, or to power electronic circuitry or devices such as calculators, radios, computers or remote monitoring or communications equipment. These power generation applications also often involve the charging of batteries or other energy storage devices so that operation may continue when direct illumination from the sun or other light sources is not available, or to balance the power output of the PV device with a specific application's requirements.

As used herein the term "resistive load" refers to any power consuming or storing circuit, device, equipment or system.

Another type of photosensitive optoelectronic device is a photoconductor cell. In this function, signal detection circuitry monitors the resistance of the device to detect changes due to the absorption of light.

Another type of photosensitive optoelectronic device is a photodetector. In operation a photodetector is used in conjunction with a current detecting circuit which measures the current generated when the photodetector is exposed to electromagnetic radiation and may have an applied bias voltage. A detecting circuit as described herein is capable of providing a bias voltage to a photodetector and measuring the electronic response of the photodetector to electromagnetic radiation.

These three classes of photosensitive optoelectronic devices may be characterized according to whether a rectifying junction as defined below is present and also according to whether the device is operated with an external applied voltage, also known as a bias or bias voltage. A photoconductor cell does not have a rectifying junction and is normally operated with a bias. A PV device has at least one rectifying junction and is operated with no bias. A photodetector has at least one rectifying junction and is usually but not always operated with a bias. Typically, a photovoltaic cell provides power to a circuit, device or equipment. A photodetector or photoconductor provides a signal or current to control detection circuitry, or the output of information from the detection circuitry but does not provide power to the circuitry, device or equipment.

Traditionally, photosensitive optoelectronic devices have been constructed of a number of inorganic semiconductors, e.g., crystalline, polycrystalline and amorphous silicon, gallium arsenide, cadmium telluride and others. Herein the term "semiconductor" denotes materials which can conduct electricity when charge carriers are induced by thermal or electromagnetic excitation. The term "photoconductive" generally relates to the process in which electromagnetic radiant energy is absorbed and thereby converted to excitation energy of electric charge carriers so that the carriers can conduct, i.e., transport, electric charge in a material. The terms "photoconductor" and "photoconductive material" are used herein to refer to semiconductor materials which are chosen for their property of absorbing electromagnetic radiation to generate electric charge carriers.

PV devices may be characterized by the efficiency with which they can convert incident solar power to useful electric power. Devices utilizing crystalline or amorphous silicon dominate commercial applications, and some have achieved efficiencies of 23% or greater. However, efficient crystalline-based devices, especially of large surface area, are difficult and expensive to produce due to the problems inherent in producing large crystals without significant efficiency-degrading defects. On the other hand, high efficiency amorphous silicon devices still suffer from problems with stability. Present commercially available amorphous silicon cells have stabilized efficiencies between 4 and 8%. More recent efforts have focused on the use of organic photovoltaic cells to achieve acceptable photovoltaic conversion efficiencies with economical production costs.

PV devices may be optimized for maximum electrical power generation under standard illumination conditions (i.e., Standard Test Conditions which are 1000 W/m$^2$, AM1.5 spectral illumination), for the maximum product of photocurrent times photovoltage. The power conversion efficiency of such a cell under standard illumination conditions depends on the following three parameters: (1) the current under zero bias, i.e., the short-circuit current $I_{SC}$, in Amperes (2) the photovoltage under open circuit conditions, i.e., the open circuit voltage $V_{OC}$, in Volts and (3) the fill factor, ff.

PV devices produce a photo-generated current when they are connected across a load and are irradiated by light. When irradiated under infinite load, a PV device generates its maximum possible voltage, V open-circuit, or $V_{OC}$. When irradiated with its electrical contacts shorted, a PV device generates its maximum possible current, I short-circuit, or $I_{SC}$. When actually used to generate power, a PV device is connected to a finite resistive load and the power output is given by the product of the current and voltage, I×V. The maximum total power generated by a PV device is inherently incapable of exceeding the product, $I_{SC} \times V_{OC}$. When the load value is optimized for maximum power extraction, the current and voltage have the values, $I_{max}$ and $V_{max}$, respectively.

A figure of merit for PV devices is the fill factor, ff, defined as:

$$f = \{I_{max}V_{max}\}/\{I_{SC}V_{OC}\} \qquad (1)$$

where ff is always less than 1, as $I_{SC}$ and $V_{OC}$ are never obtained simultaneously in actual use. Nonetheless, as ff approaches 1, the device has less series or internal resistance and thus delivers a greater percentage of the product of $I_{SC}$ and $V_{OC}$ to the load under optimal conditions. Where $P_{inc}$ is the power incident on a device, the power efficiency of the device, $\eta_P$, may be calculated by:

$$\eta_P = ff^*(I_{SC}^*V_{OC})/P_{inc}$$

To produce internally generated electric fields which occupy a substantial volume, the usual method is to juxtapose two layers of material with appropriately selected conductive properties, especially with respect to their distribution of molecular quantum energy states. The interface of these two materials is called a photovoltaic heterojunction. In traditional semiconductor theory, materials for forming PV heterojunctions have been denoted as generally being of either n or p type. Here n-type denotes that the majority carrier type is the electron. This could be viewed as the material having many electrons in relatively free energy states. The p-type denotes that the majority carrier type is the hole. Such material has many holes in relatively free energy states. The type of the background, i.e., not photo-generated, majority carrier concentration depends primarily on unintentional doping by defects or impurities. The type and concentration of impurities determine the value of the Fermi energy, or level, within the gap between the highest occupied molecular orbital (HOMO) energy level and the lowest unoccupied molecular orbital (LUMO) energy level, called the HOMO-LUMO gap. The Fermi energy characterizes the statistical occupation of molecular quantum energy states denoted by the value of energy for which the probability of occupation is equal to ½. A Fermi energy near the LUMO energy level indicates that electrons are the predominant carrier. A Fermi energy near the HOMO energy level indicates that holes are the predominant carrier. Accordingly, the Fermi energy is a primary characterizing property of traditional semiconductors and the prototypical PV heterojunction has traditionally been the p-n interface.

The term "rectifying" denotes, inter alia, that an interface has an asymmetric conduction characteristic, i.e., the interface supports electronic charge transport preferably in one direction. Rectification is associated normally with a built-in electric field which occurs at the heterojunction between appropriately selected materials.

The current-voltage characteristics of organic heterojunctions are often modeled using the generalized Shockley equation derived for inorganic diodes. However, since the Shockley equation does not rigorously apply to organic semiconductor donor-acceptor (D-A) heterojunctions (HJs), the extracted parameters lack a clear physical meaning.

In the context of organic materials, the terms "donor" and "acceptor" refer to the relative positions of the HOMO and LUMO energy levels of two contacting but different organic materials. This is in contrast to the use of these terms in the inorganic context, where "donor" and "acceptor" may refer to types of dopants that may be used to create inorganic n- and p-types layers, respectively. In the organic context, if the LUMO energy level of one material in contact with another is lower, then that material is an acceptor. Otherwise it is a donor. It is energetically favorable, in the absence of an external bias, for electrons at a donor-acceptor junction to move into the acceptor material, and for holes to move into the donor material.

A significant property in organic semiconductors is carrier mobility. Mobility measures the ease with which a charge carrier can move through a conducting material in response to an electric field. In the context of organic photosensitive devices, a layer including a material that conducts preferentially by electrons due to a high electron mobility may be referred to as an electron transport layer, or ETL. A layer including a material that conducts preferentially by holes due to a high hole mobility may be referred to as a hole transport layer, or HTL. In one embodiment, an acceptor material is an ETL and a donor material is a HTL.

Conventional inorganic semiconductor PV cells employ a p-n junction to establish an internal field. Early organic thin film cell, such as reported by Tang, *Appl. Phys Lett.* 48, 183 (1986), contain a heterojunction analogous to that employed in a conventional inorganic PV cell. However, it is now recognized that in addition to the establishment of a p-n type junction, the energy level offset of the heterojunction also plays an important role. The energy level offset at the organic D-A heterojunction is believed to be important to the operation of organic PV devices due to the fundamental nature of the photogeneration process in organic materials. Upon optical excitation of an organic material, localized Frenkel or charge-transfer excitons are generated. For electrical detection or current generation to occur, the bound excitons must be dissociated into their constituent electrons and holes. Such a process can be induced by the built-in electric field, but the efficiency at the electric fields typically found in organic devices (F~$10^6$ V/cm) is low. The most efficient exciton dissociation in organic materials occurs at a donor-acceptor (D-A) interface. At such an interface, the donor material with a low ionization potential forms a heterojunction with an acceptor material with a high electron affinity. Depending on the alignment of the energy levels of the donor and acceptor materials, the dissociation of the exciton can become energetically favorable at such an interface, leading to a free electron polaron in the acceptor material and a free hole polaron in the donor material.

Organic PV cells have many potential advantages when compared to traditional silicon-based devices. Organic PV cells are light weight, economical in materials use, and can be deposited on low cost substrates, such as flexible plastic foils. However, organic PV devices typically have relatively low external quantum efficiency (electromagnetic radiation to electricity conversion efficiency), being on the order of 1% or less. This is, in part, thought to be due to the second order nature of the intrinsic photoconductive process. That is, carrier generation requires exciton generation, diffusion and ionization or collection. There is an efficiency η associated with each of these processes. Subscripts may be used as follows: P for power efficiency, EXT for external quantum efficiency, A for photon absorption exciton generation, ED for diffusion, CC for collection, and INT for internal quantum efficiency. Using this notation:

$$\eta_P \sim \eta_{EXT} = \eta_{ED}^* \eta_{CC}$$

$$\eta_{EXT} = \eta_A^* \eta_{INT}$$

The diffusion length ($L_D$) of an exciton is typically much less ($L_D$~50Å) than the optical absorption length (~500Å), requiring a tradeoff between using a thick, and therefore resistive, cell with multiple or highly folded interfaces, or a thin cell with a low optical absorption efficiency.

Linear acenes such as tetracene and pentacene have received much attention in recent years for use as semiconductors in organic field-effect transistors (OFETs) or in organic PV applications due to their favorable absorption and packing behavior. These materials possess absorption bands in the UV and visible region of the spectrum. Substituents are often added to increase solubility and control the packing behavior in a crystal or thin film. The majority of the work on linear acenes, such as tetracene and pentacene, as semiconductors has focused on the use of these materials to transport holes as p-type materials. In recent years, good hole carrier mobilities have been achieved. Very few linear tetracenes and pentacenes, however, have been reported with n-type properties.

Recent approaches to achieve n-type properties in tetracene and pentacene derivatives have focused on substituting the acene core with electron withdrawing groups such as halogens and nitriles. Other strategies have focused on the incorporation of nitrogen into the acene. Theoretical calculations, as shown in FIG. 1, indicate that by replacing CH's with N's in the acene, the HOMO-LUMO gap can be systematically lowered. This strategy for the development of aza-rich acenes with n-type properties has been severely hindered due to the difficulties in synthesis. Current strategies for aza-acene synthesis rely on the use of condensation chemistry using o-diaminoarenes as starting materials. The two major disadvantages with this route are (1) o-diaminoarenes are not simple starting materials or easy to functionalize to provide access to a large number of derivatives, and (2) Bunz et al. have shown that aza-acenes prepared with this route can be problematic to oxidize. Thus, there remains a need to fabricate new aza-acenes using novel synthesis.

Disclosed herein are methods of synthesizing aza-acenes, such as aza-tetracenes, comprising the step of aromatizing a compound having a general formula selected from

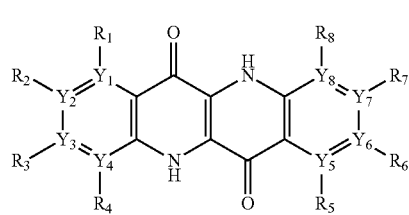

I

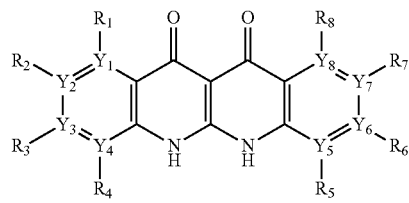

II

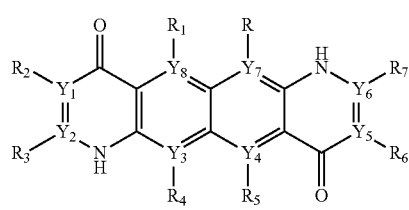

III

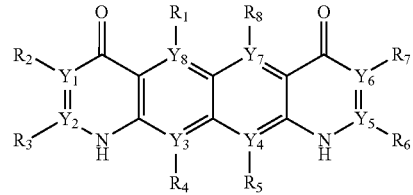

IV

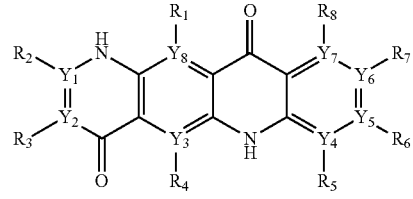

V

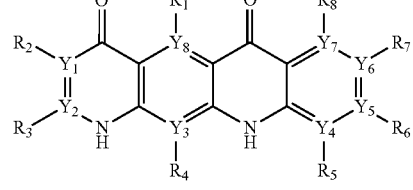

VI wherein $Y_n$ are independently selected from C and N, and $R_n$ are independently selected from saturated carbocyclic, saturated heterocyclic, unsaturated carbocyclic, and unsaturated heterocyclic rings with adjacent $R_n$, a H, an aryl, a halide, a pseudohalide, an alkyl, and an electron acceptor with the proviso that any of $R_n$ is H when the Y to which it is bonded is N.

Also disclosed are methods of synthesizing aza-acenes, such as aza-pentacenes, comprising the step of aromatizing a compound having a general formula selected from

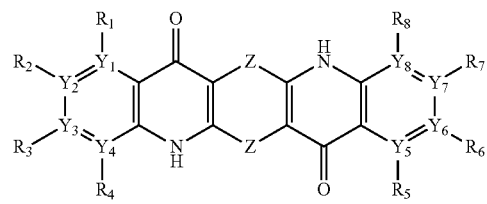

VII

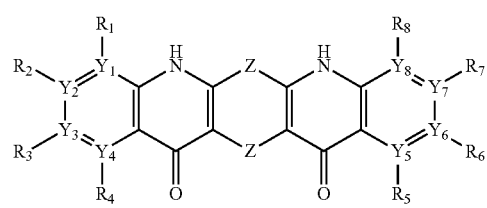

VIII

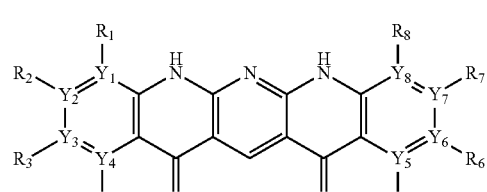

IX

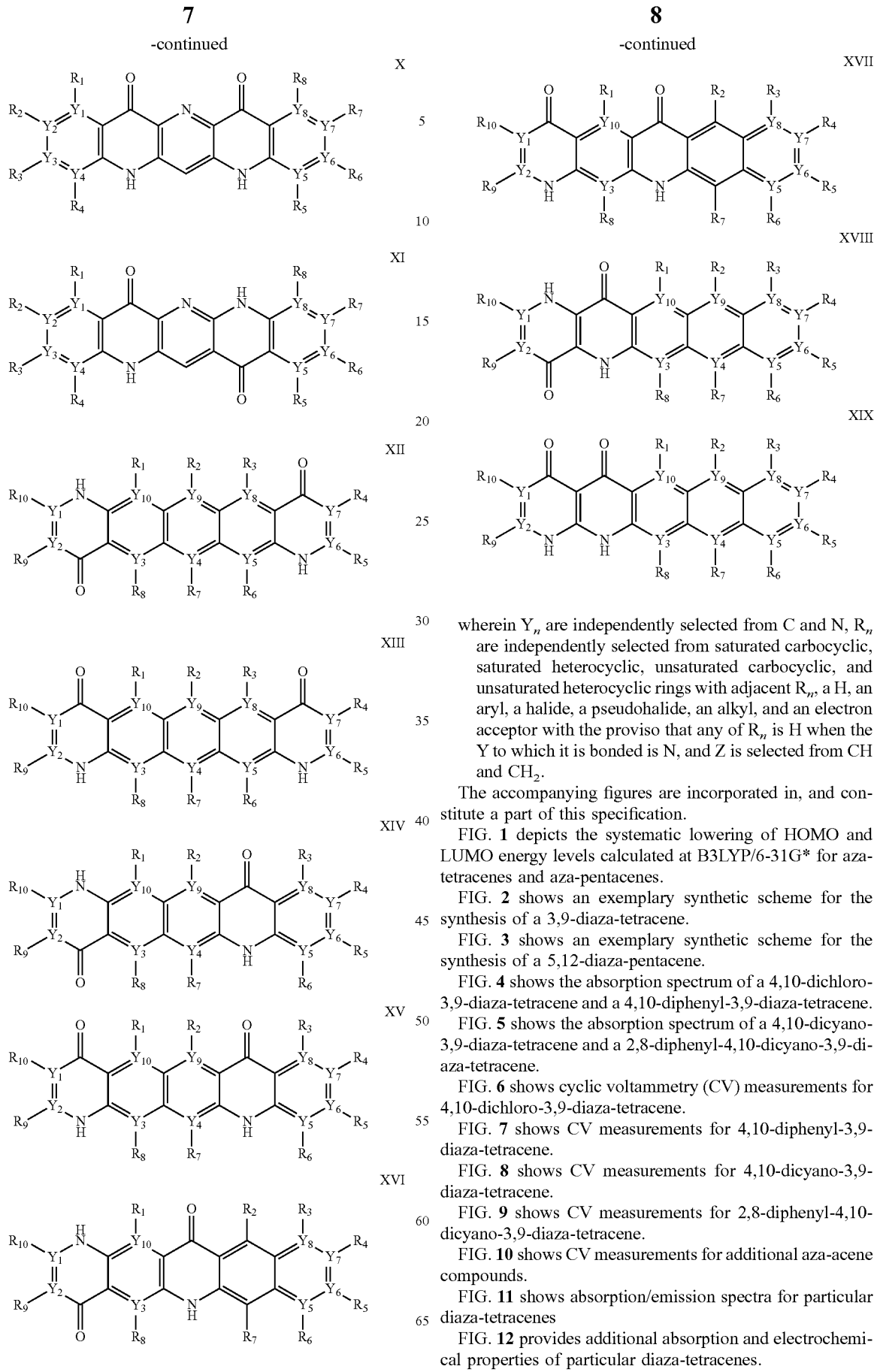

wherein $Y_n$ are independently selected from C and N, $R_n$ are independently selected from saturated carbocyclic, saturated heterocyclic, unsaturated carbocyclic, and unsaturated heterocyclic rings with adjacent $R_n$, a H, an aryl, a halide, a pseudohalide, an alkyl, and an electron acceptor with the proviso that any of $R_n$ is H when the Y to which it is bonded is N, and Z is selected from CH and $CH_2$.

The accompanying figures are incorporated in, and constitute a part of this specification.

Figure 12:
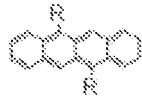
Figure 12:
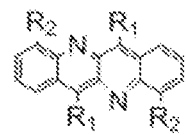

FIG. 12 provides additional absorption and electrochemical properties of particular diaza-tetracenes.

Figure 13:
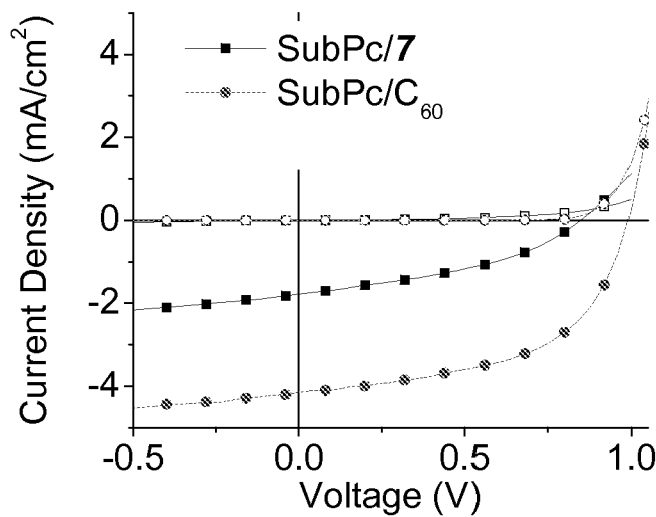

FIG. 13 shows current density-vs.-voltage characteristics for OPV devices employing a particular diaza-tetracene as an acceptor material.

As described herein, aza-acenes may be synthesized by aromatizing a compound selected from I through XIX. In some embodiments, the compound selected from I through XIX is aromatized with a treatment comprising an oxyphilic reagent. The oxyphilic reagent may be, for example, phosphoryl trichloride (POCl$_3$), phosphoryl tribromide (POBr$_3$), phosphorous tribromide (PBr$_3$), pentachloro-phosphorane (PCl$_5$), phosphorous trichloride (PCl$_3$), tetrabenzyl pyrophosphate, 1-dibenzyl phosphite, phenyldichlorophosphate, and thionyl chloride (SOCl$_2$). In certain embodiments, the oxyphilic reagent is POCl$_3$. In this embodiment, the compound selected from I through XIX undergoes a deoxygenation-chlorination reaction to yield the corresponding dichloro-aza-acene, which can be subjected to further transformation to yield desired substituents.

In other embodiments, the compound selected from I through XIX is aromatized by bonding a protective group to the quinolone nitrogens followed by treatment with a reagent selected from alkyl or aryl organolithium reagents and alkyl or aryl Grignard reagents. In some embodiments, the protective group is MEM, although persons of ordinary skill in the art would recognize that other protective groups may be used. The protective group on the quinolone nitrogen allows treatment with alkyl or aryl organolithium reagents or alkyl or aryl Grignard reagents to yield the desired aza-acenes. The synthesis of compounds I through XIX may rely on the use of anilines or derivatives thereof as primary starting materials. Anilines are much simpler starting materials compared to o-diaminoarenes, and as a result they provide a greater number of potential derivatives that can be accessed. Another advantage of the present invention is the use of POCl$_3$ to aromatize compounds I through XIX to aza-acenes. This avoids any problems in oxidation chemistry, as quinolone residues have previously been shown to aromatize with POCl$_3$. A compound selected from I though XIX may also be synthesized using aminopyridines or derivatives thereof. The significance of these materials is found in the ability to incorporate nitrogen into every ring of acenes, such as tetracene and pentacene.

There are a variety of approaches to form the carbon-nitrogen bond between an aromatic amine and an aryl-halide. The most common methods are those involving Cu and Pd catalyst, specifically Ullmann or Buchwald-Hartwig conditions. Another approach may use the acid catalyzed condensation chemistry using aromatic-amines which is the traditional route in forming the bond in the synthesis of both epindolidione and quinacridone. The carbon-nitrogen bond formation is not limited to these approaches. For example, Conrad-Limpach cyclization has been demonstrated from a variety of carbonyl functionalities mostly from carboxylic acids, amides and thio-esters; however, other functionalities may also be suitable. The cyclization conditions are typically carried out in hot polyphosphoric acid (PPA) but are not limited to this reagent as the reaction can occur through a pure thermal process or through the aid of other strong acids.

In one embodiment of the present invention, a method of synthesizing a compound selected from aza-tetracenes comprises the step of aromatizing a compound selected from I through VI.

In one embodiment, the compound to be synthesized is selected from

1
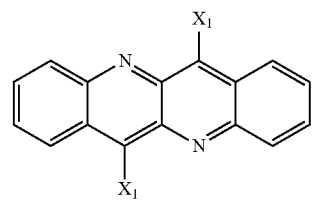

2
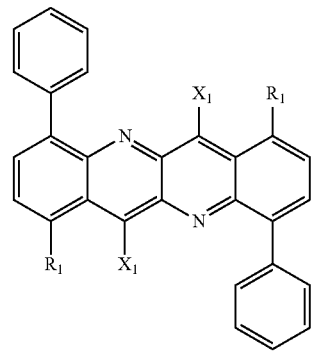

3
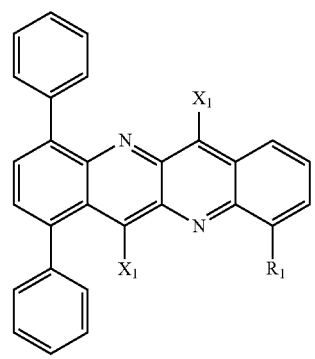

4
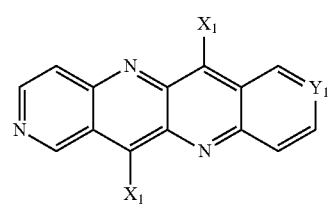

5
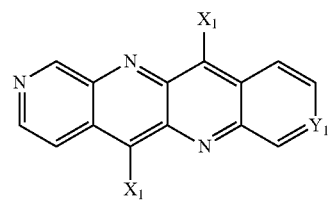

6
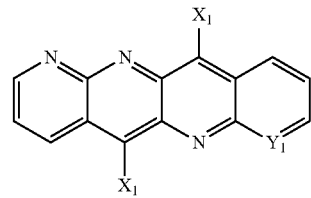

-continued
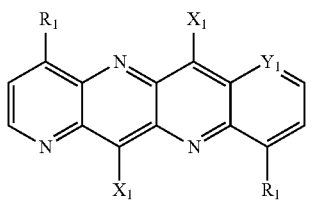
7
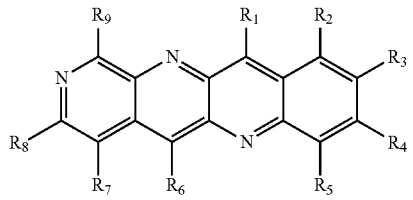
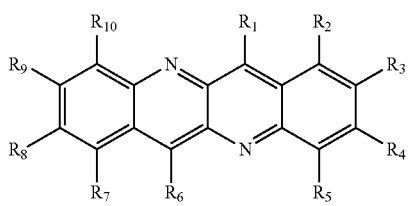
8
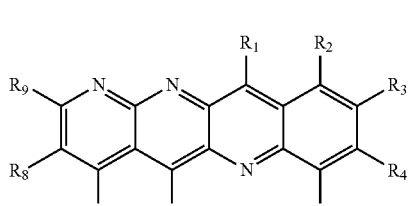
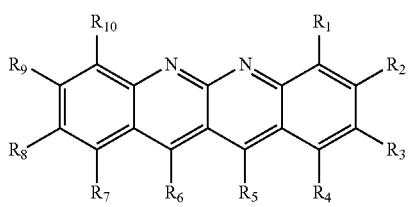
9
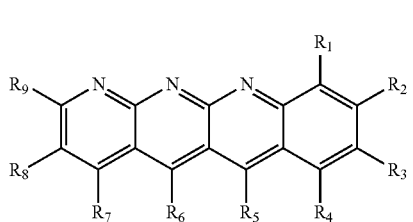
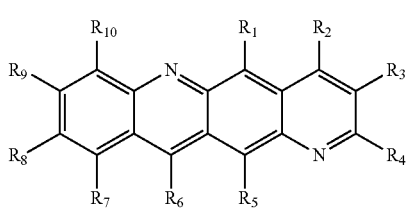
10
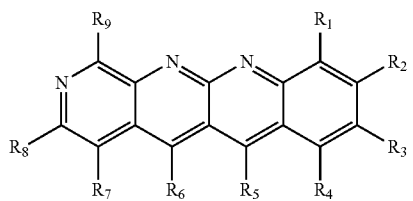
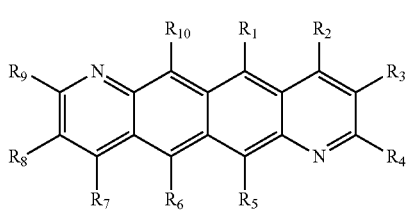
11
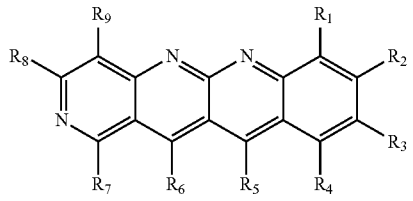
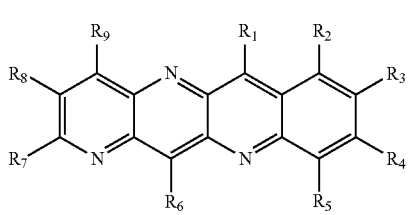
12
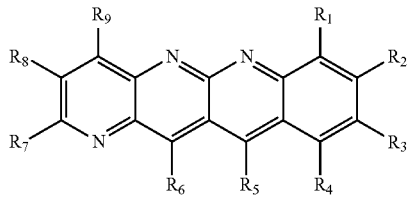
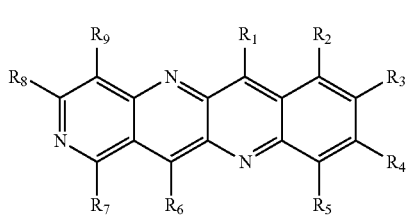
13
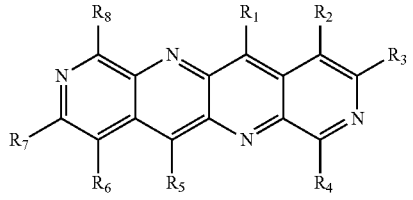

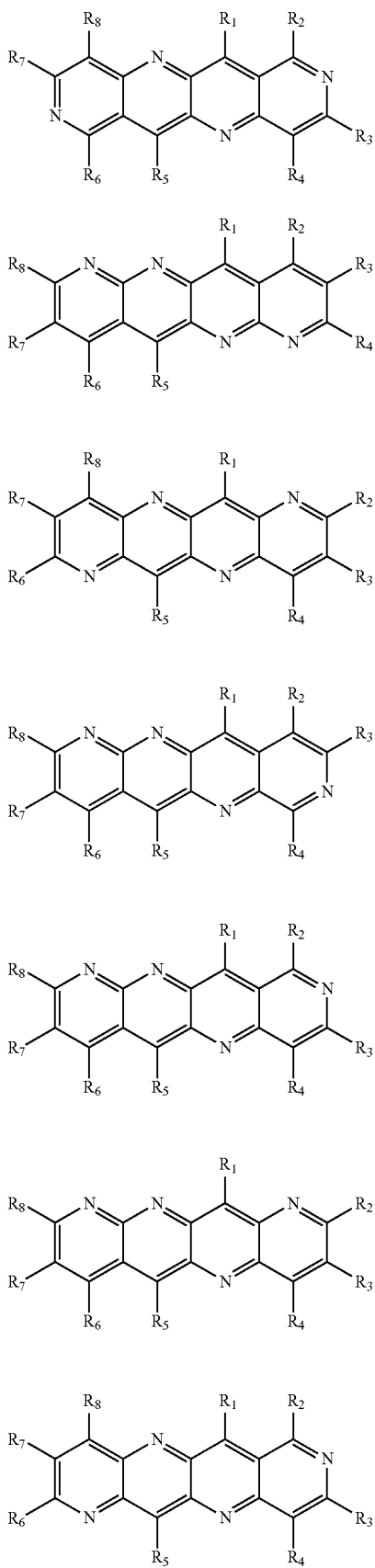

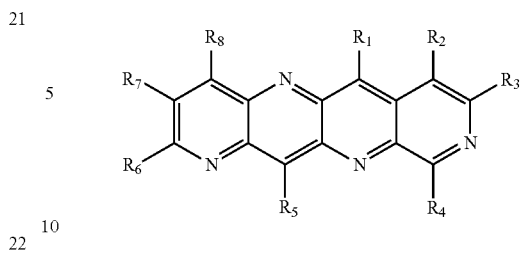

wherein X₁ and Rₙ are independently selected from saturated carbocyclic, saturated heterocyclic, unsaturated carbocyclic, and unsaturated heterocyclic rings with adjacent Rₙ, a H, an aryl, a halide, a pseudohalide, an alkyl, and an electron acceptor, and Y₁ is selected from CH and N.

In some embodiments, the compound selected from I through VI is aromatized with a treatment comprising an oxyphilic reagent as described herein. In other embodiments, the compound selected from I through VI is aromatized by bonding a protective group to the quinolone nitrogens followed by treatment with a reagent selected from alkyl or aryl organolithium reagents and alkyl or aryl Grignard reagents as described herein.

In some embodiments, the compound to be synthesized is selected from aza-tetracenes, wherein the method of synthesizing further comprises the step of synthesizing a compound selected from I through VI, wherein $Y_n$ is C. In some embodiments, the compound selected from I through VI, wherein $Y_n$ is C, is synthesized using an aniline or a derivative thereof having a general formula

A

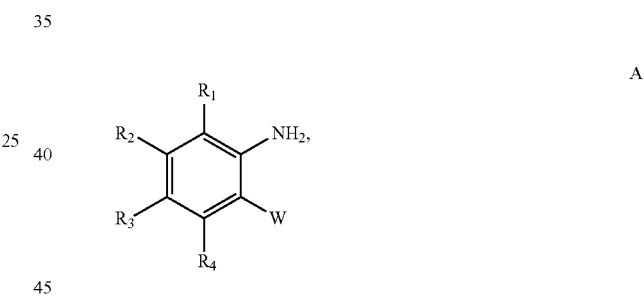

wherein $R_{1-4}$ are independently selected from saturated carbocyclic, saturated heterocyclic, unsaturated carbocyclic, and unsaturated heterocyclic rings with adjacent $R_n$, a H, an aryl, a halide, a pseudohalide, an alkyl, and an electron acceptor, and W is selected from H, —CO₂H, —CO₂R, —COSR, and —CONR₂. As one of ordinary skill in the art would appreciate, desired substituents on the aza-acenes may be achieved by using particular anilines or derivatives thereof as starting materials.

A diaza-tetracene aromatized from an exemplary compound of compound I may be synthesized, for example, based on the following reaction scheme:

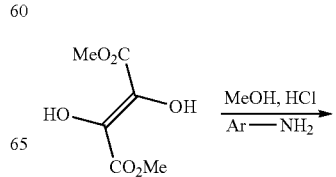

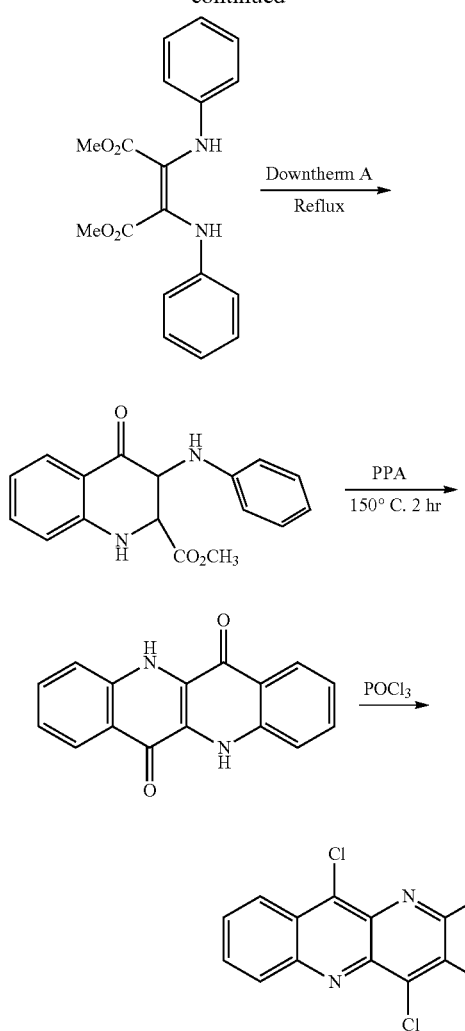

A diaza-tetracene aromatized from an exemplary compound of compound II may be synthesized, for example, based on the following reaction scheme:

A diaza-tetracene aromatized from an exemplary compound of compound II may also be synthesized, for example, based on the following reaction scheme:

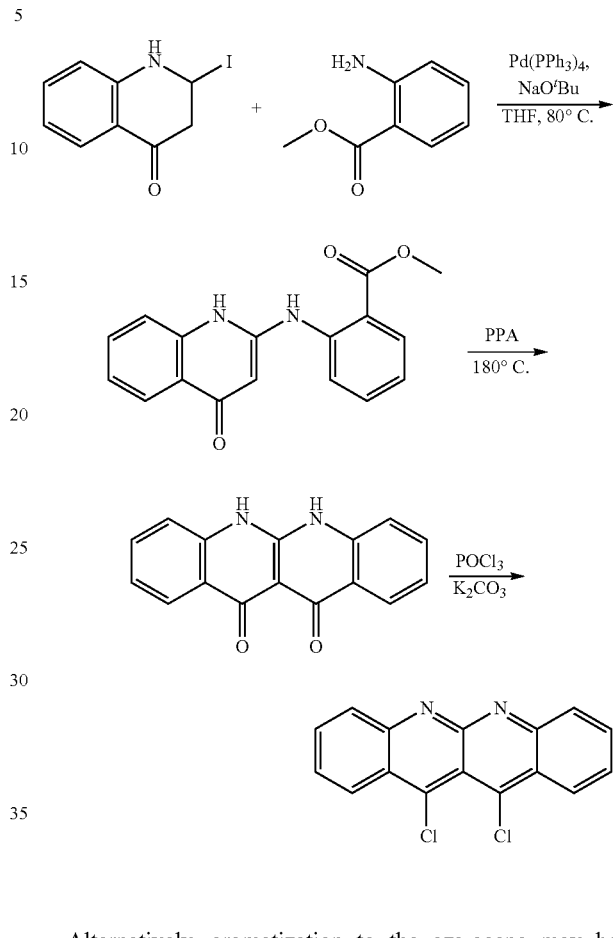

Alternatively, aromatization to the aza-acene may be accomplished by bonding a protective group to the quinolone nitrogens followed by treatment with a reagent selected from alkyl or aryl organolithium reagents and alkyl or aryl Grignard reagents as described herein. The following reaction scheme provides an example of using MEM-Cl to protect the quinolone nitrogens followed by treatment with an aryl Grignard reagent:

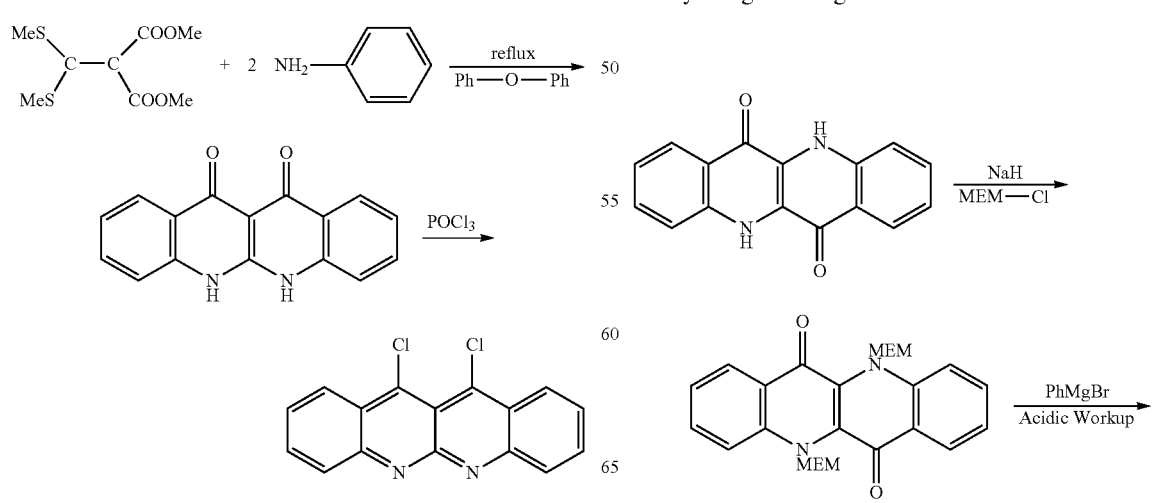

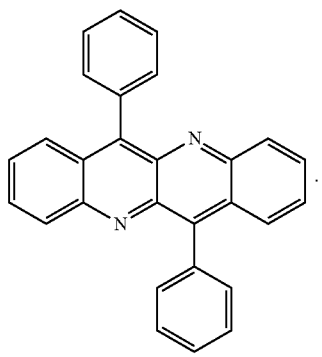

A diaza-tetracene aromatized from an exemplary compound of compound III may be synthesized, for example, based on the following reaction scheme:

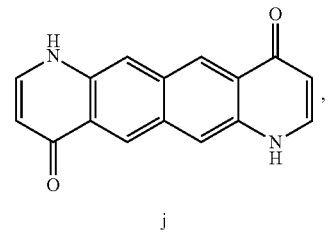

j wherein the resulting compound j may be aromatized by an oxyphilic reagent as described herein, or aromatized by bonding a protective group to the quinolone nitrogens followed by treatment with a reagent selected from alkyl or aryl organolithium reagents and alkyl or aryl Grignard reagents as described herein.

A diaza-tetracene aromatized from an exemplary compound of compound VI may be synthesized, for example, based on the following reaction scheme:

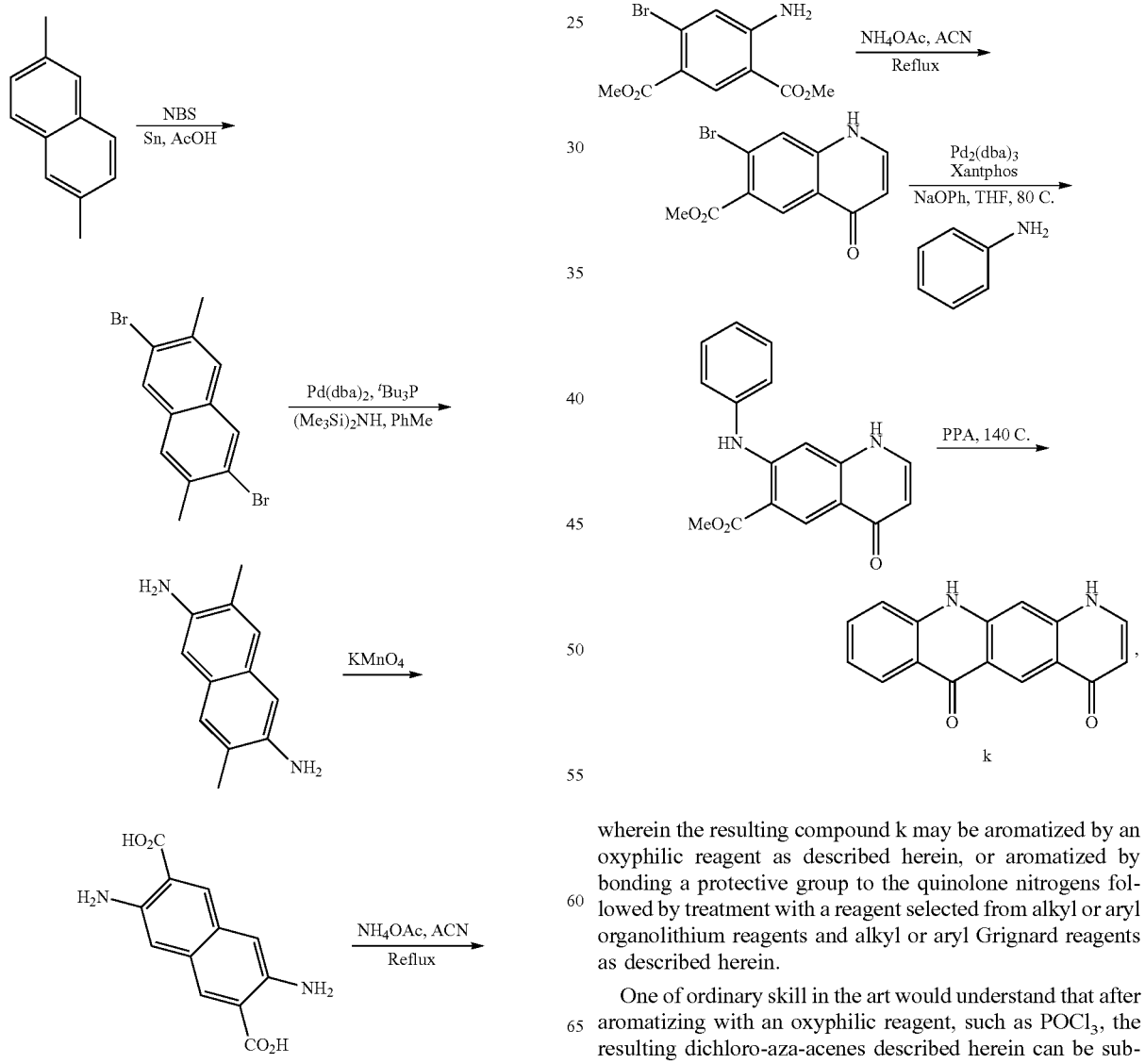

k wherein the resulting compound k may be aromatized by an oxyphilic reagent as described herein, or aromatized by bonding a protective group to the quinolone nitrogens followed by treatment with a reagent selected from alkyl or aryl organolithium reagents and alkyl or aryl Grignard reagents as described herein.

One of ordinary skill in the art would understand that after aromatizing with an oxyphilic reagent, such as POCl$_3$, the resulting dichloro-aza-acenes described herein can be subject to further transformations to yield desired substituents.

In one embodiment, the aza-tetracene to be synthesized is a diaza-tetracene selected from 1
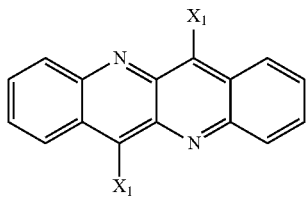

2
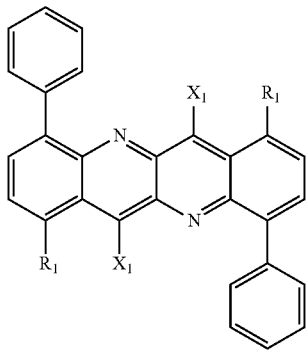

3
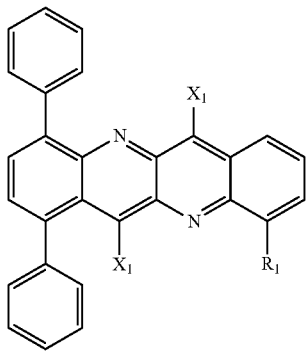

8
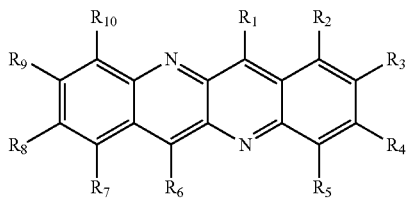

9
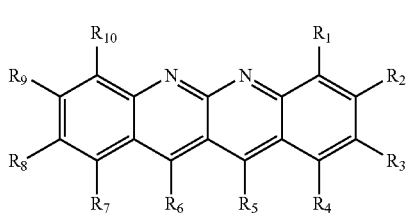

10
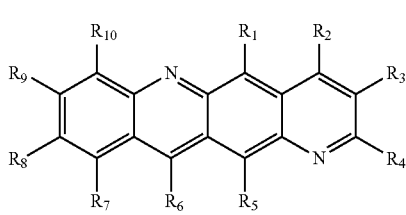

-continued

11
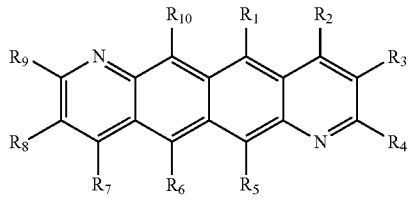

wherein $X_1$ and $R_n$ are independently selected from saturated carbocyclic, saturated heterocyclic, unsaturated carbocyclic, and unsaturated heterocyclic rings with adjacent $R_n$, a H, an aryl, a halide, a pseudohalide, an alkyl, and an electron acceptor.

Aza-tetracenes having 3 or more nitrogens in their cores, such as triaaza-tetracene and tetraaza-tetracene may be obtained by using an aminopyridine or a derivative thereof in place of aniline or a derivative thereof. Aminopyridines or derivatives thereof may also be used in conjunction with anilines or derivatives thereof on a step-by-step basis to obtain aza-acenes having 3 or more nitrogens in their cores. Thus, in some embodiments, the compound to be synthesized is selected from aza-tetracenes, wherein the method of synthesizing further comprises the step of synthesizing a compound selected from I through VI. In some embodiments, the compound selected from I through VI is synthesized using an aminopyridine or a derivative thereof having a general formula selected from

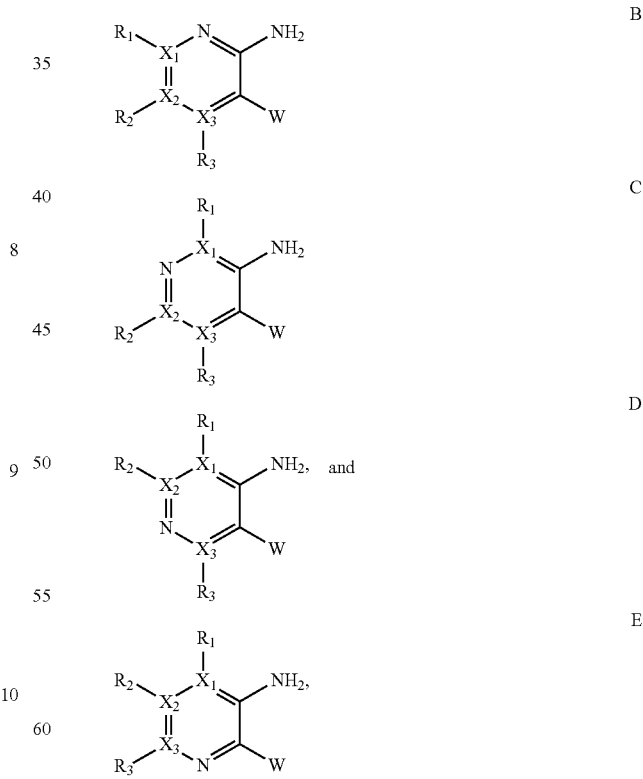

wherein $X_{1-3}$ are independently selected from N and C, $R_{1-3}$ are independently selected from saturated carbocyclic, saturated heterocyclic, unsaturated carbocyclic, and unsaturated heterocyclic rings with adjacent $R_n$, a H, an aryl, a halide, a pseudohalide, an alkyl, and an electron acceptor, with the proviso that any of $R_{1-3}$ is H when the X to which it is bonded is N, and W is selected from H, —$CO_2H$, —$CO_2R$, —COSR, and —$CONR_2$. As one of ordinary skill in the art would appreciate, the particular aminopyridine or derivative thereof that is used will affect the positions of the nitrogens in the aza-acenes, as well as the substituents on the aza-acenes.

A tetraaza-tetracene aromatized from an exemplary compound of compound I, may be synthesized based on, for example, the following reaction scheme:

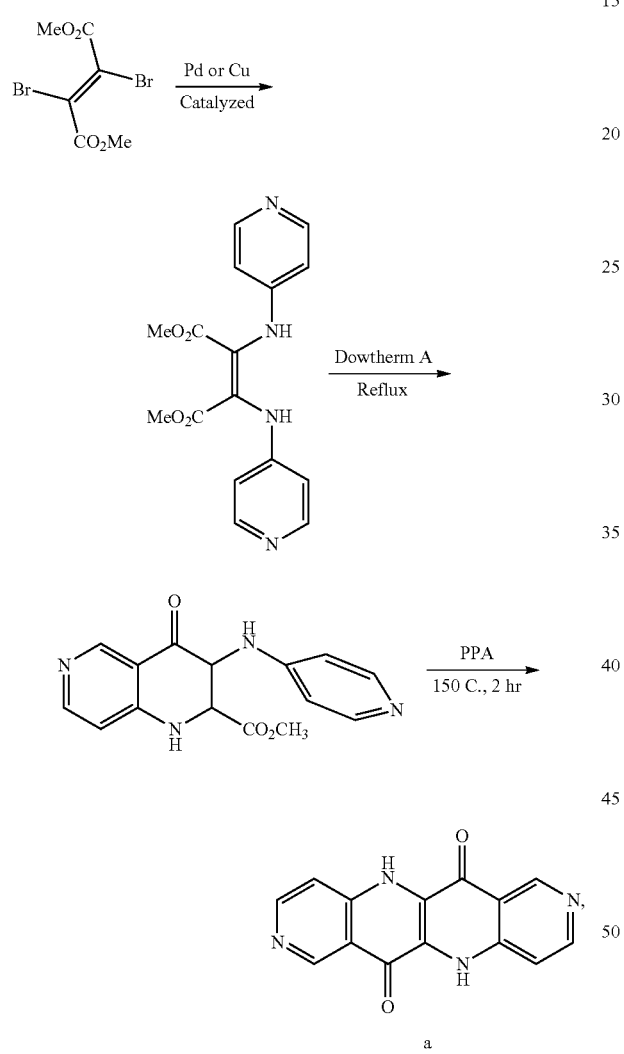

a wherein the resulting compound a may be aromatized by an oxyphilic reagent as described herein, or aromatized by bonding a protective group to the quinolone nitrogens followed by treatment with a reagent selected from alkyl or aryl organolithium reagents and alkyl or aryl Grignard reagents as described herein.

Triaza-tetracenes aromatized from exemplary compounds of compounds I and II may be synthesized by unsymmetrical syntheses based on, for example, the following schemes:

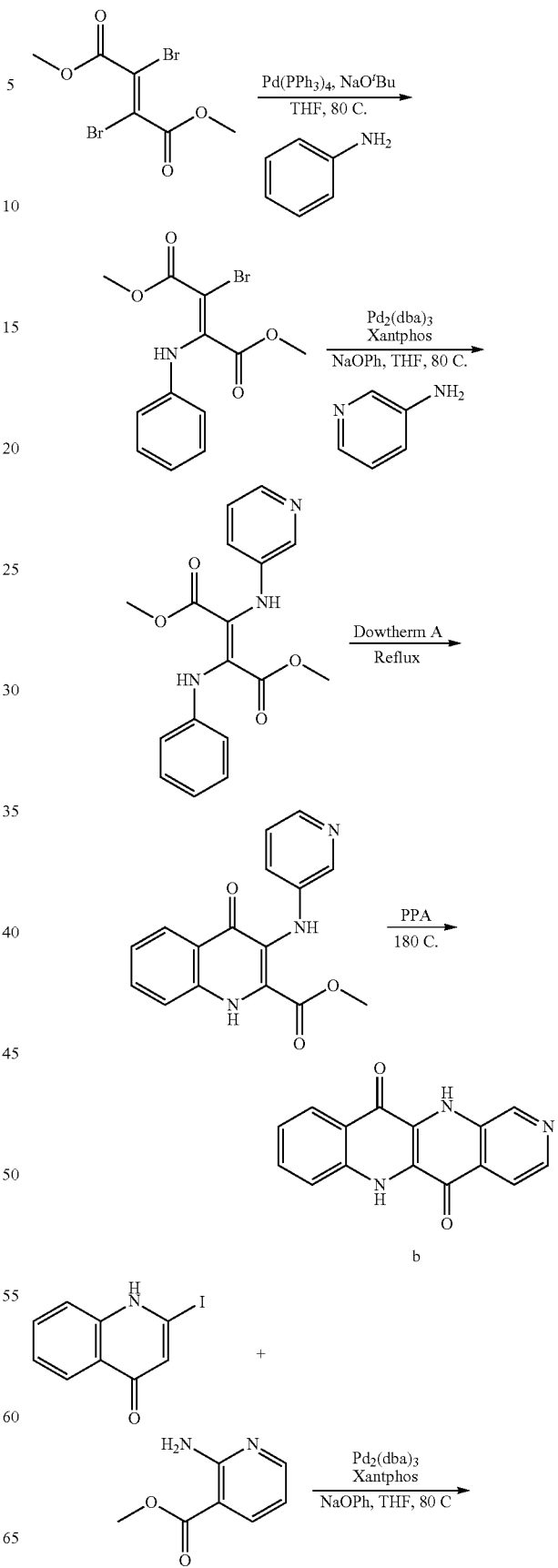

b

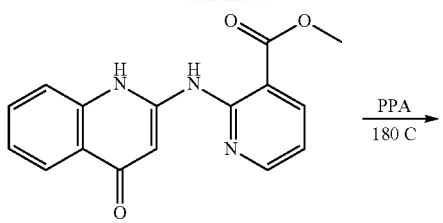

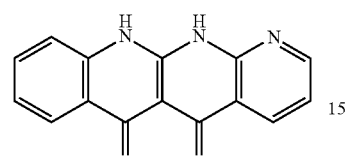

wherein the resulting compounds b and c may be aromatized by an oxyphilic reagent as described herein, or aromatized by bonding a protective group to the quinolone nitrogens followed by treatment with a reagent selected from alkyl or aryl organolithium reagents and alkyl or aryl Grignard reagents as described herein.

In one embodiment, the aza-tetracene to be synthesized is a triaza-tetracene or tetraaza-tetracene selected from

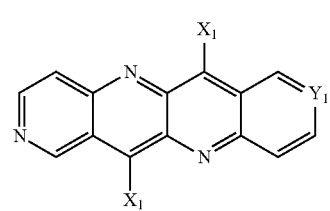

4

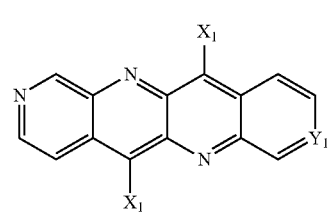

5

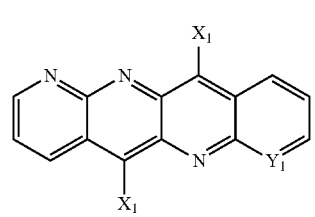

6

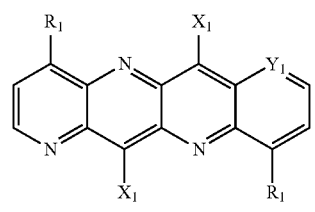

7

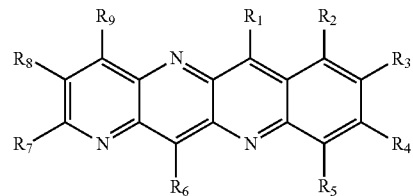

12

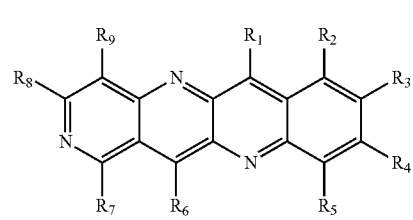

13

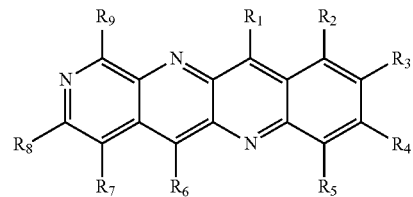

14

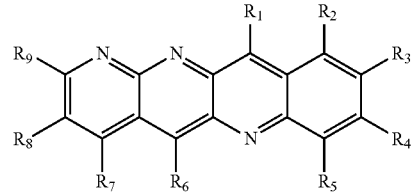

15

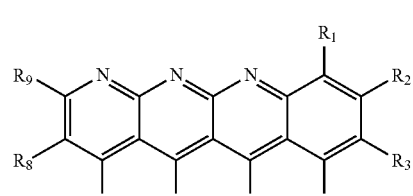

16

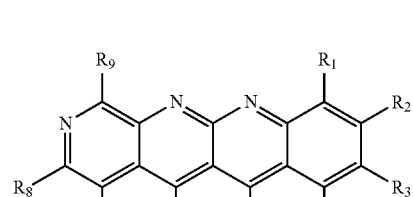

17

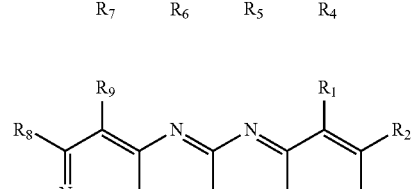

18

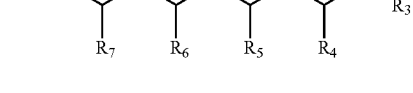

-continued

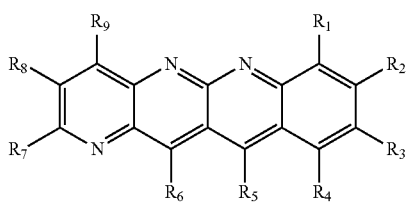

19

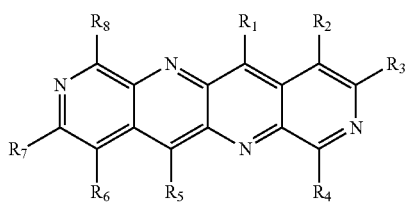

20

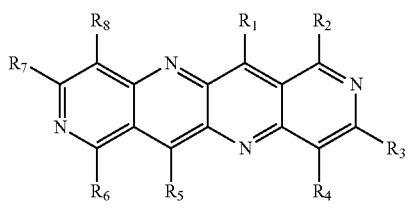

21

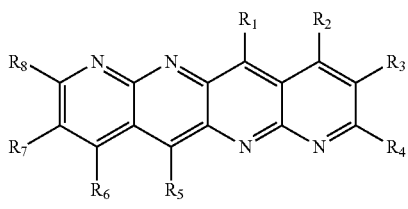

22

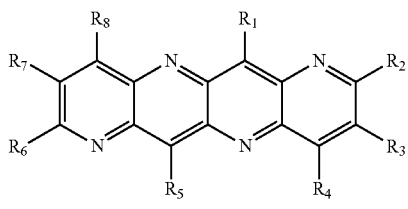

23

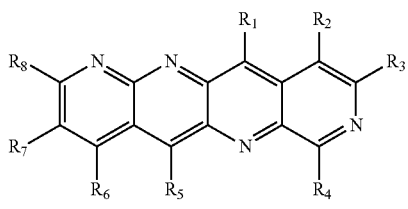

24

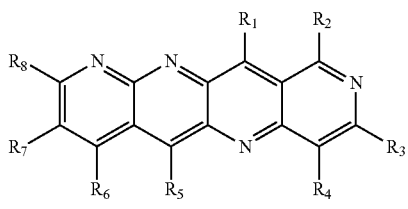

25

-continued

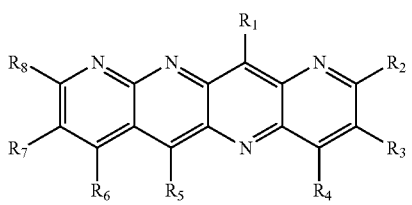

26

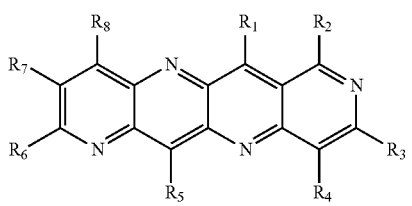

27

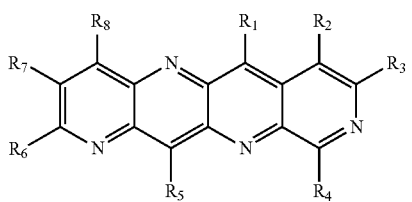

28 wherein $X_1$ and $R_n$ are independently selected from saturated carbocyclic, saturated heterocyclic, unsaturated carbocyclic, and unsaturated heterocyclic rings with adjacent $R_n$, a H, an aryl, a halide, a psuedohalide, an alkyl, and an electron acceptor, and $Y_1$ is selected from CH and N.

In another embodiment of the present invention, a method of synthesizing a compound selected from aza-pentacenes, comprises the step of aromatizing a compound selected from compounds VII through XIX.

In one embodiment, the compound is selected from

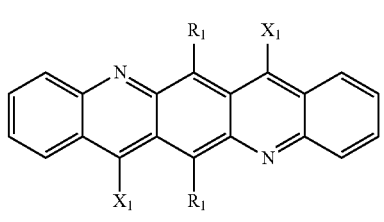

29

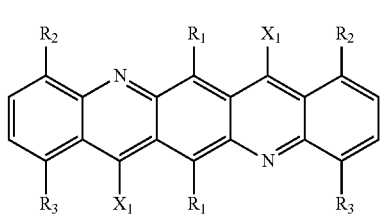

30

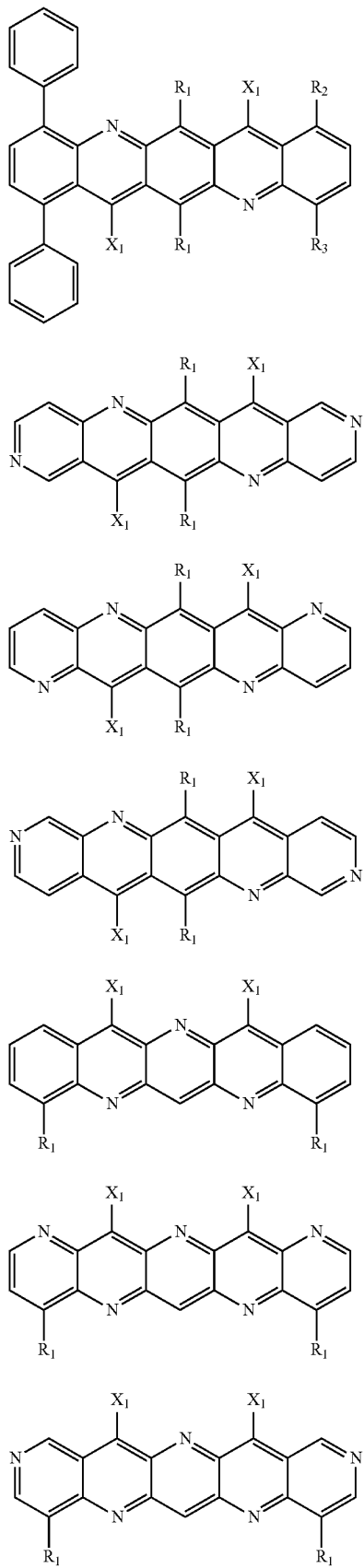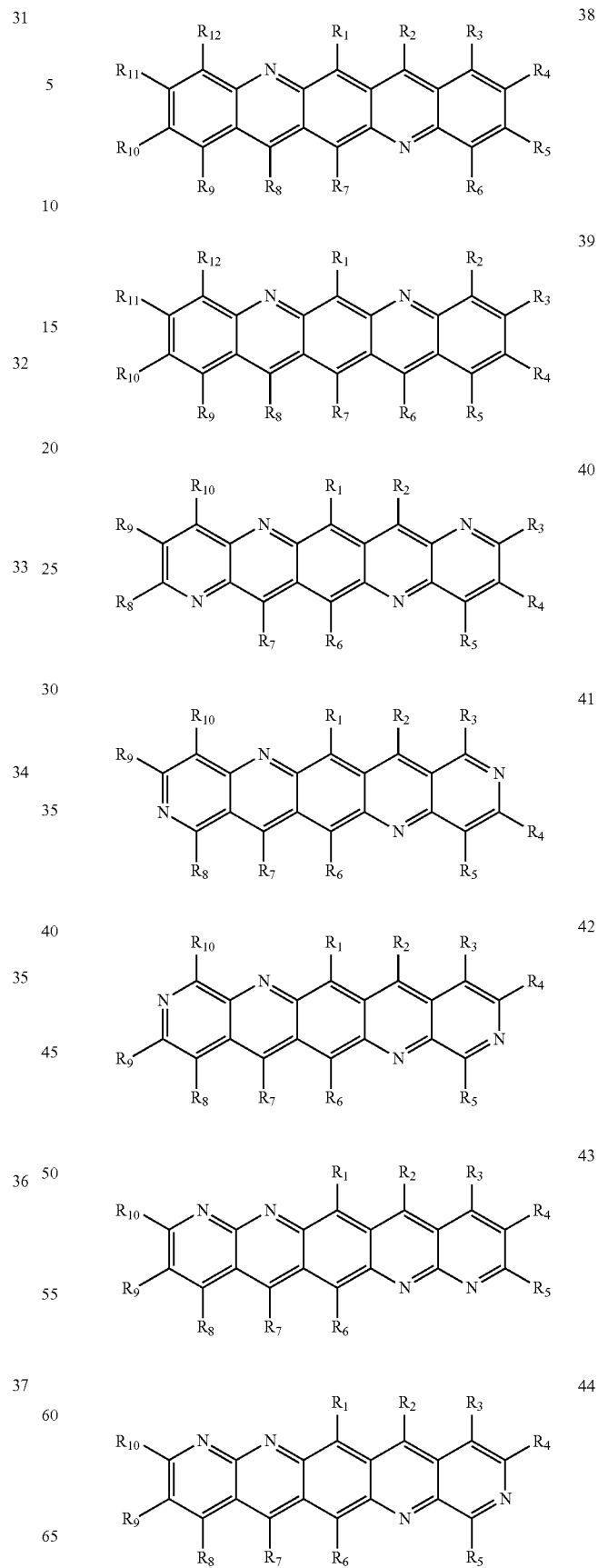

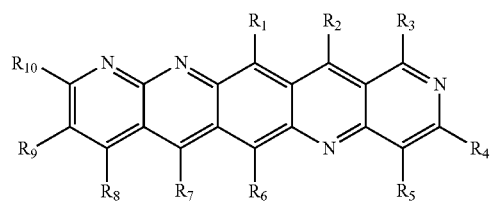
45
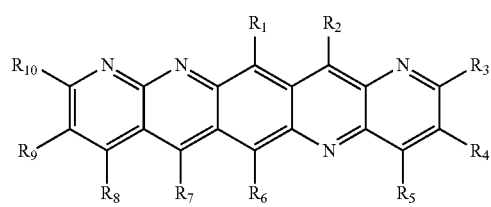
46
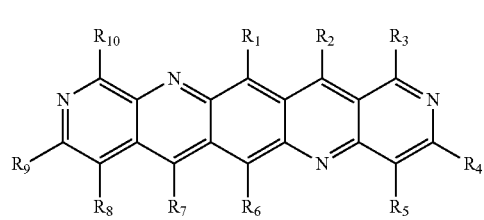
47
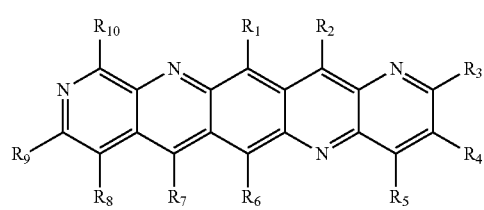
48
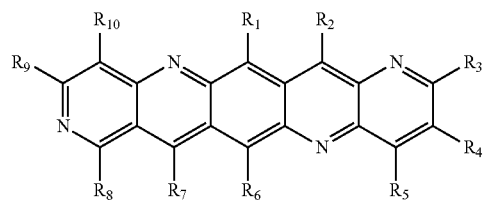
49
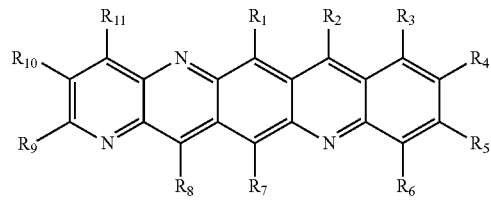
50
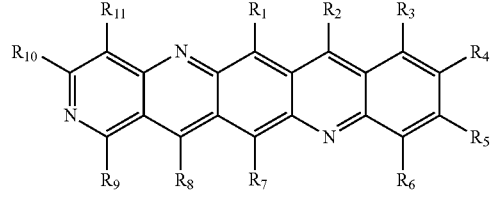
51
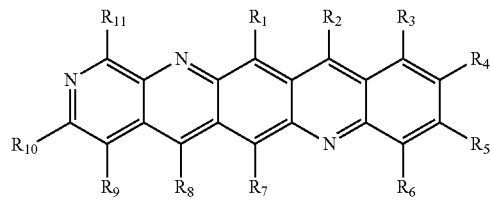
52
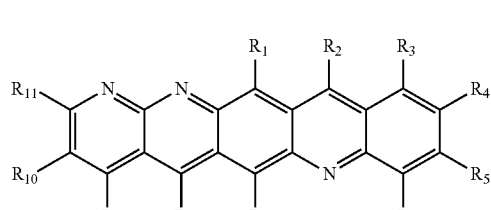
53
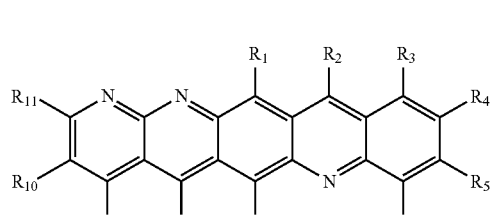
54
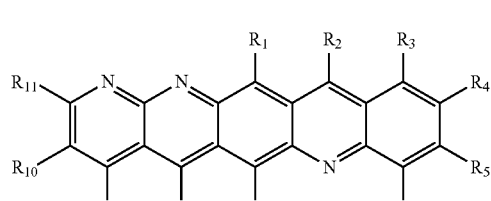
55
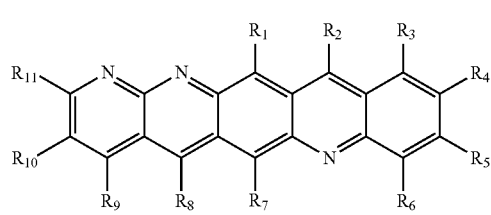
56
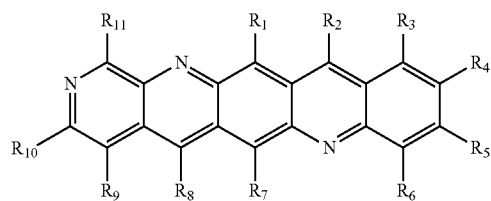
57
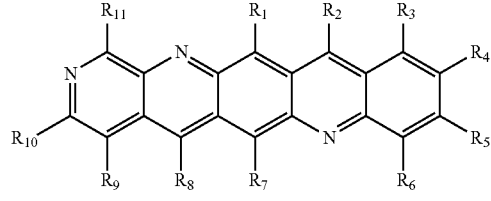
58

-continued
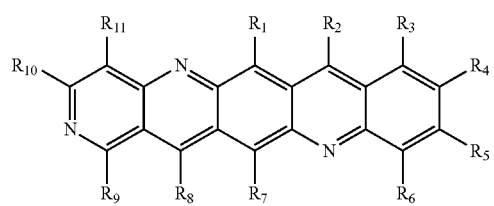
59
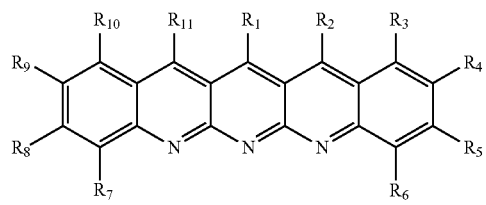
60
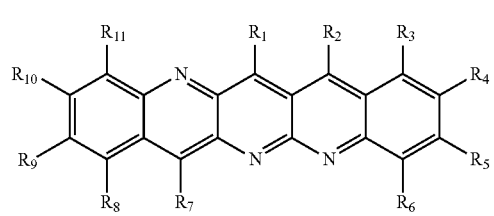
61
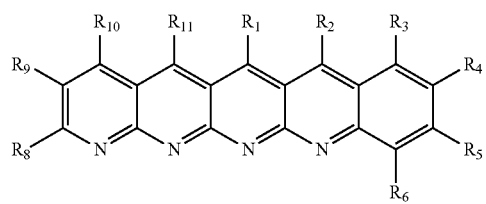
62
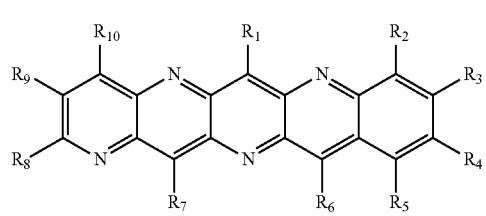
63
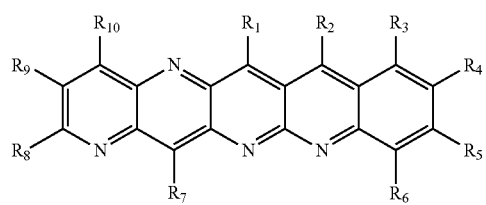
64
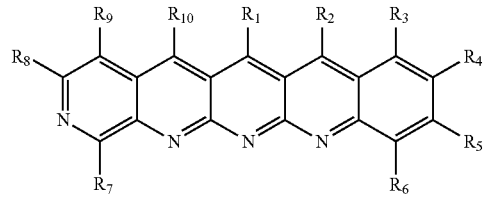
65
-continued
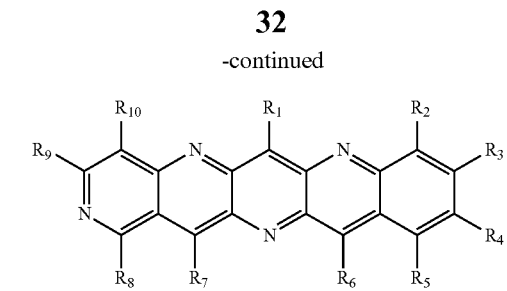
66
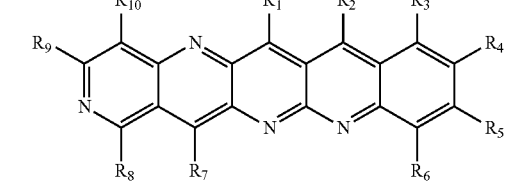
67
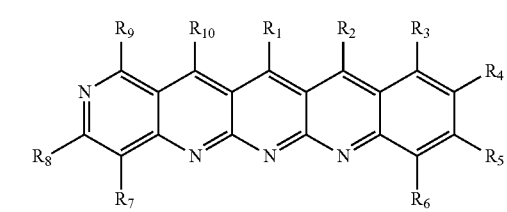
68
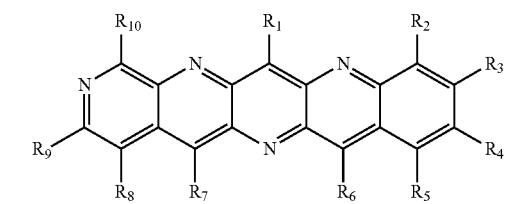
69
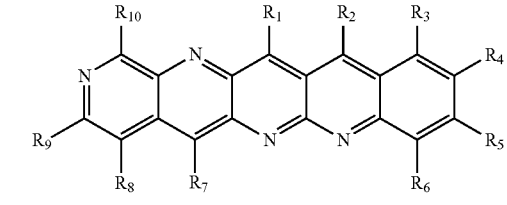
70
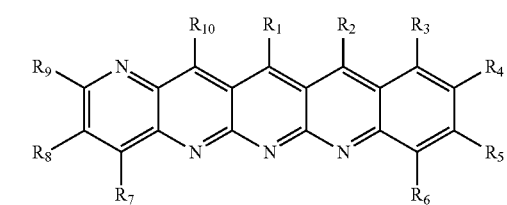
71
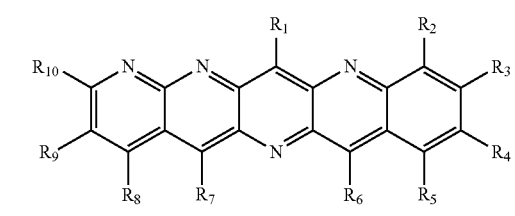
72

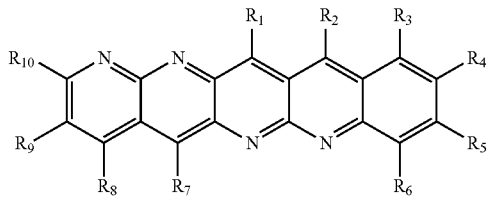

wherein $X_1$ and $R_n$ are independently selected from saturated carbocyclic, saturated heterocyclic, unsaturated carbocyclic, and unsaturated heterocyclic rings with adjacent $R_n$, a H, an aryl, a halide, a pseudohalide, an alkyl, and an electron acceptor.

In some embodiments, the compound selected from VII through XIX is aromatized with a treatment comprising an oxyphilic reagent as described herein. In other embodiments, the compound selected from VII through XIX is aromatized by bonding a protective group to the quinolone nitrogens followed by treatment with a reagent selected from alkyl or aryl organolithium reagents and alkyl or aryl Grignard reagents as described herein.

In some embodiments, the compound to be synthesized is selected from aza-pentacenes, wherein the method of synthesizing further comprises the step of synthesizing a compound selected from VII through XIX, wherein $Y_n$ is C. In some embodiments, the compound selected from VII through XIX, wherein $Y_n$ is C, is synthesized using an aniline or a derivative thereof having a general formula

A

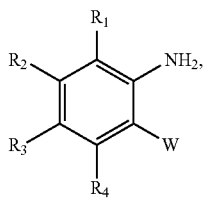

wherein $R_{1-4}$ are independently selected from saturated carbocyclic, saturated heterocyclic, unsaturated carbocyclic, and unsaturated heterocyclic rings with adjacent $R_n$, a H, an aryl, a halide, a pseudohalide, an alkyl, and an electron acceptor, and W is selected from H, —$CO_2H$, —$CO_2R$, —COSR, and —$CONR_2$.

A diaza-pentacene aromatized from exemplary compounds of compound VII, may be synthesized, for example, based on the following schemes:

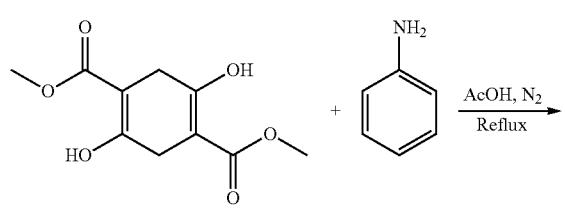

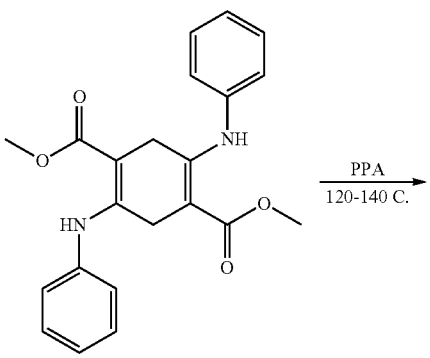

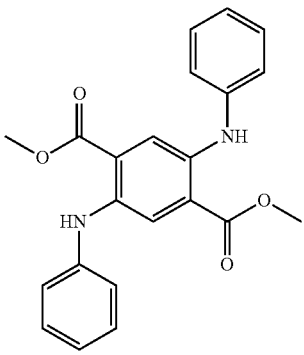

d

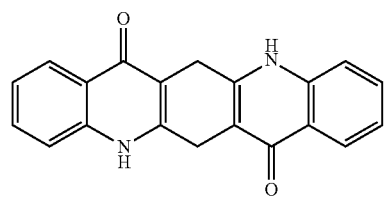

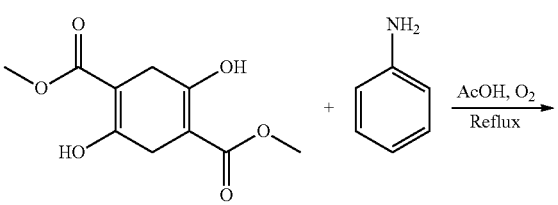

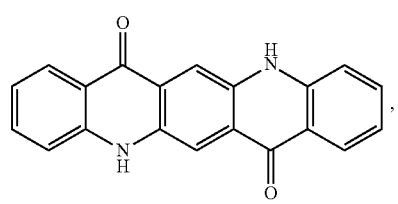

e wherein the resulting compounds d and e may be aromatized by an oxyphilic reagent as described herein, or aromatized by bonding a protective group to the quinolone nitrogens followed by treatment with a reagent selected from alkyl or aryl organolithium reagents and alkyl or aryl Grignard reagents as described herein. The following reaction scheme provides an example of using MEM-Cl to protect the quinolone nitrogen followed by treatment with an aryl Grignard reagent:

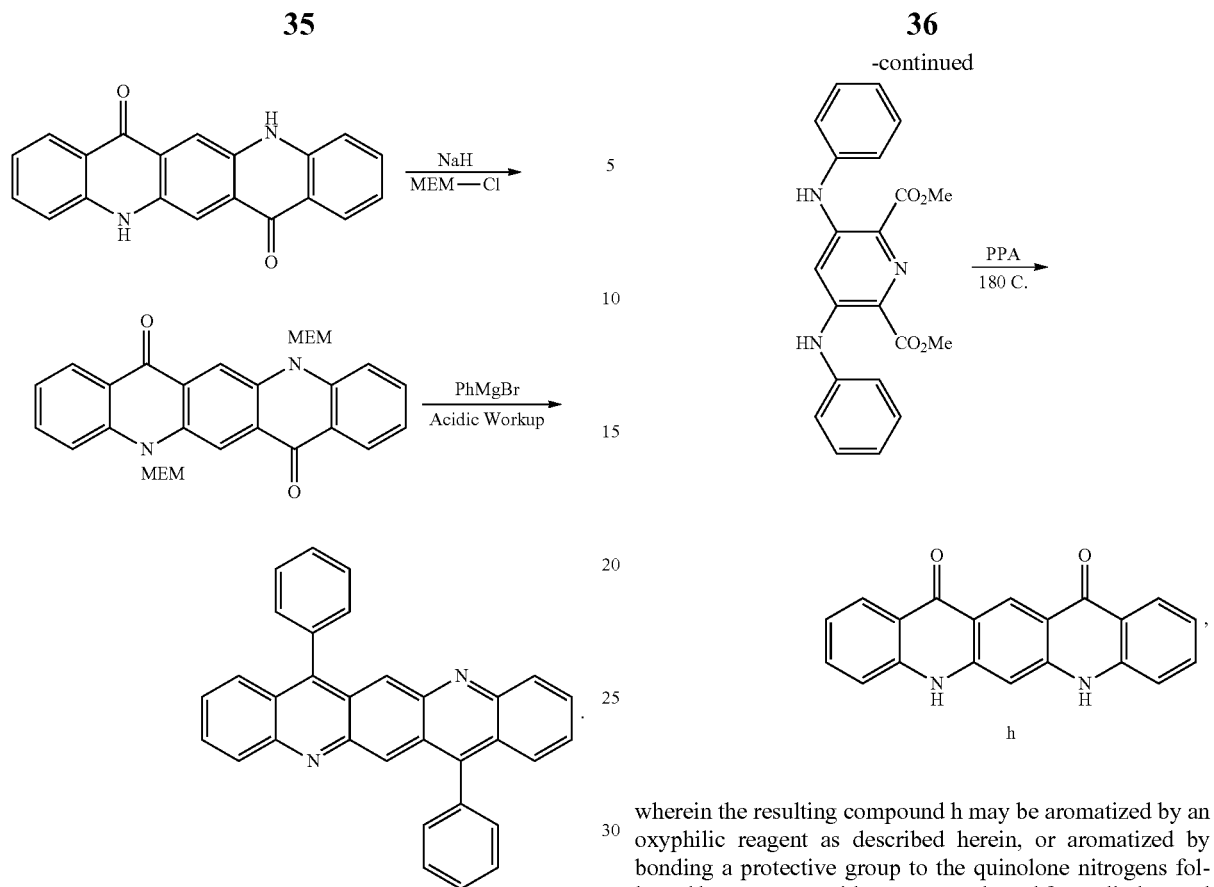

A diaza-pentacene aromatized from an exemplary compound of compound VIII may be synthesized, for example, based on the following reaction scheme:

wherein the resulting compound h may be aromatized by an oxyphilic reagent as described herein, or aromatized by bonding a protective group to the quinolone nitrogens followed by treatment with a reagent selected from alkyl or aryl organolithium reagents and alkyl or aryl Grignard reagents as described herein.

A diaza-pentacene aromatized from an exemplary compound of compound XII, may be synthesized, for example, based on the following reaction scheme:

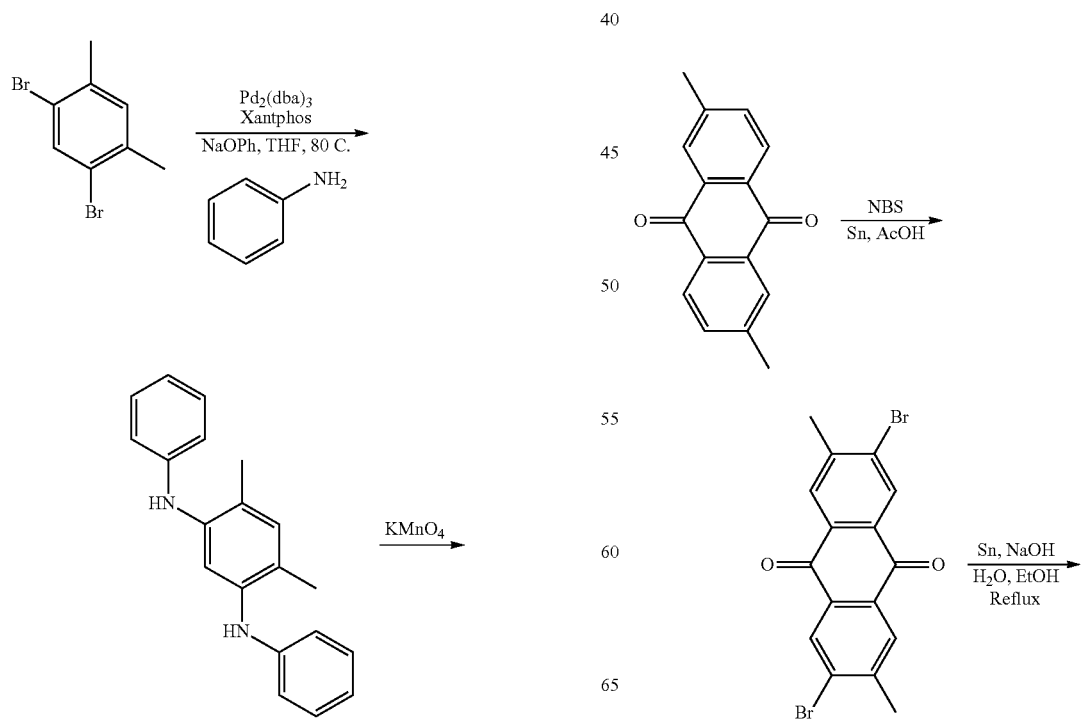

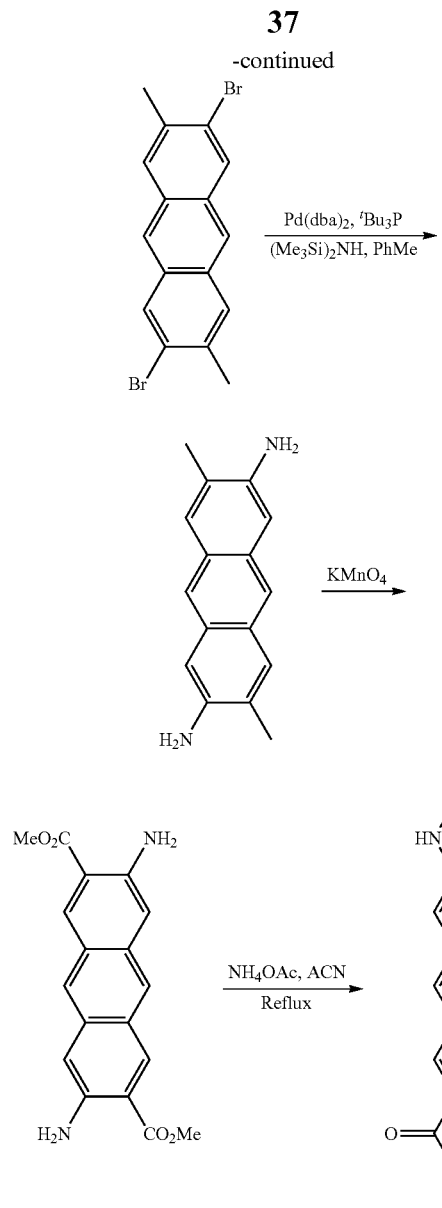

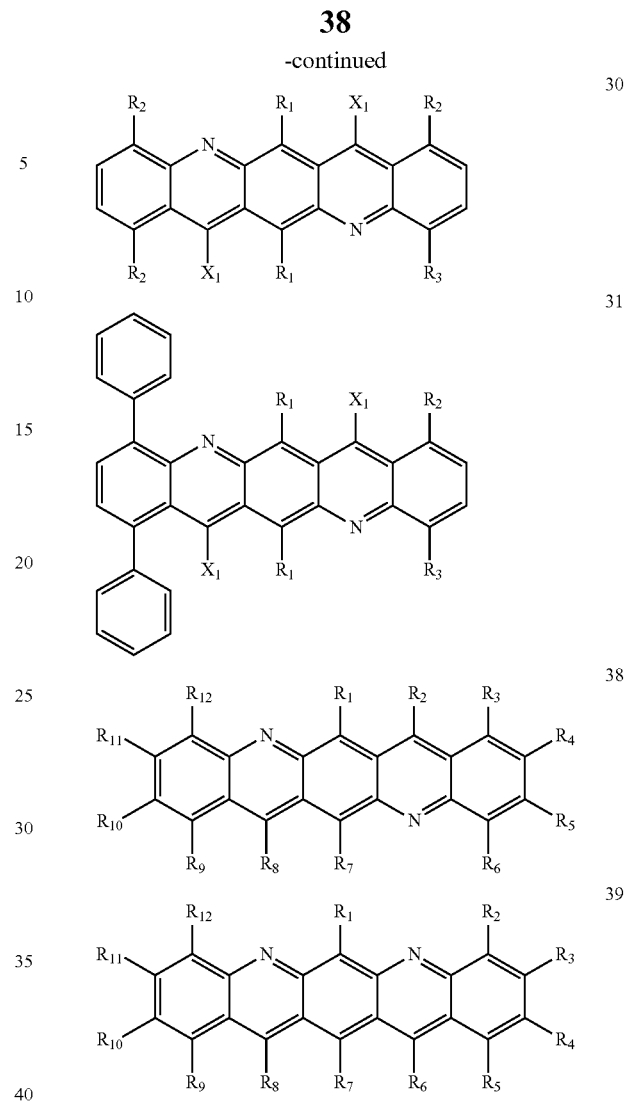

wherein the resulting compound m may be aromatized by an oxyphilic reagent as described herein, or aromatized by bonding a protective group to the quinolone nitrogens followed by treatment with a reagent selected from alkyl or aryl organolithium reagents and alkyl or aryl Grignard reagents as described herein.

In one embodiment, the aza-pentacene to be synthesized is a diaza-pentacene selected from

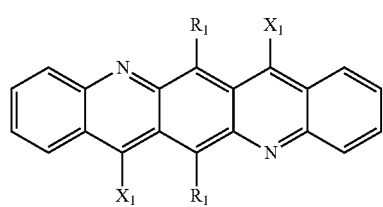

wherein $X_1$ and $R_n$ are independently selected from saturated carbocyclic, saturated heterocyclic, unsaturated carbocyclic, and unsaturated heterocyclic rings with adjacent $R_n$, a H, an aryl, a halide, a psuedohalide, an alkyl, and an electron acceptor.

Aza-pentacenes having 3 or more nitrogens in their cores, such as triaza-pentacenes, tetraaza-pentacenes, and pentaaza-pentacenes, may be obtained in some instances by using aminopyridines or derivatives thereof in place of anilines or derivatives thereof. Aminopyridine or a derivative thereof may also be used in conjunction with aniline or a derivative thereof on a step-by-step basis to obtain aza-pentacenes having 3 or more nitrogens in their cores. Aniline or a derivative thereof, aminopyridine or a derivative thereof, and pyridine derivatives, or combinations thereof may also be used as starting materials to obtain aza-pentacenes having 3 or more nitrogens in their cores. Thus, in some embodiments, the compound to be synthesized is selected from aza-pentacenes, wherein the method of synthesizing further comprises the step of synthesizing a compound selected from compounds VII through XIX. In some embodiments, the compound selected from VII through XIX is synthesized using an aminopyridine or a derivative thereof having a general formula selected from

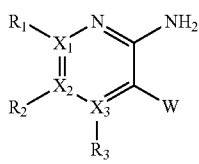

B

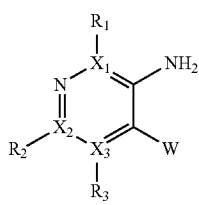

C

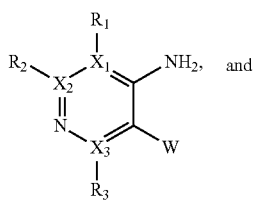

D

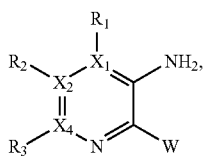

E wherein $X_{1-3}$ are independently selected from N and C, $R_{1-3}$ are independently selected from saturated carbocyclic, saturated heterocyclic, unsaturated carbocyclic, and unsaturated heterocyclic rings with adjacent $R_n$, a H, an aryl, a halide, a pseudohalide, an alkyl, and an electron acceptor, with the proviso that any of $R_{1-3}$ is H when the X to which it is bonded is N, and W is selected from H, —$CO_2H$, —$CO_2R$, —COSR, and —$CONR_2$. As one of ordinary skill in the art would appreciate, the particular aminopyridine or derivative thereof that is used will affect the number and position of the nitrogens in the aza-acenes, as well as the substituents on the aza-acenes.

A triaza-pentacene aromatized from an exemplary compound of compound VII, may be synthesized based on, for example, the following reaction scheme:

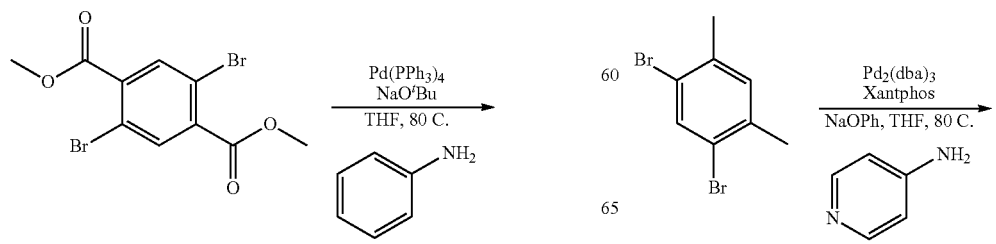

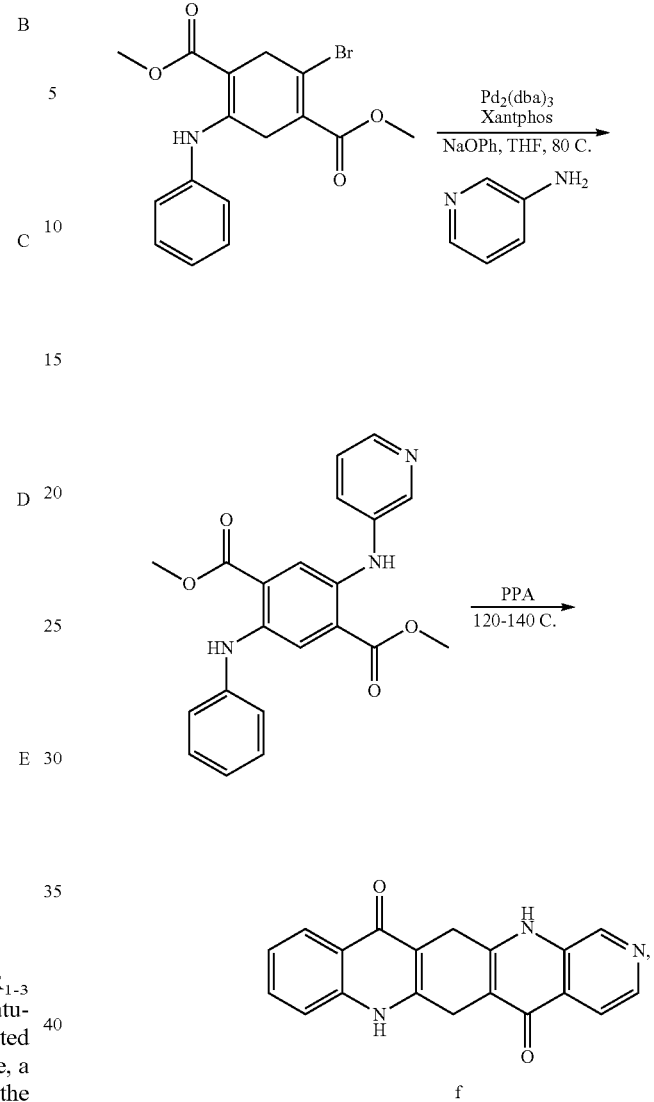

wherein the resulting compound f may be aromatized by an oxyphilic reagent as described herein, or aromatized by bonding a protective group to the quinolone nitrogens followed by treatment with a reagent selected from alkyl or aryl organolithium reagents and alkyl or aryl Grignard reagents as described herein.

A tetraaza-pentacene aromatized from an exemplary compound of compound VIII, may be synthesized based on, for example, the following reaction scheme:

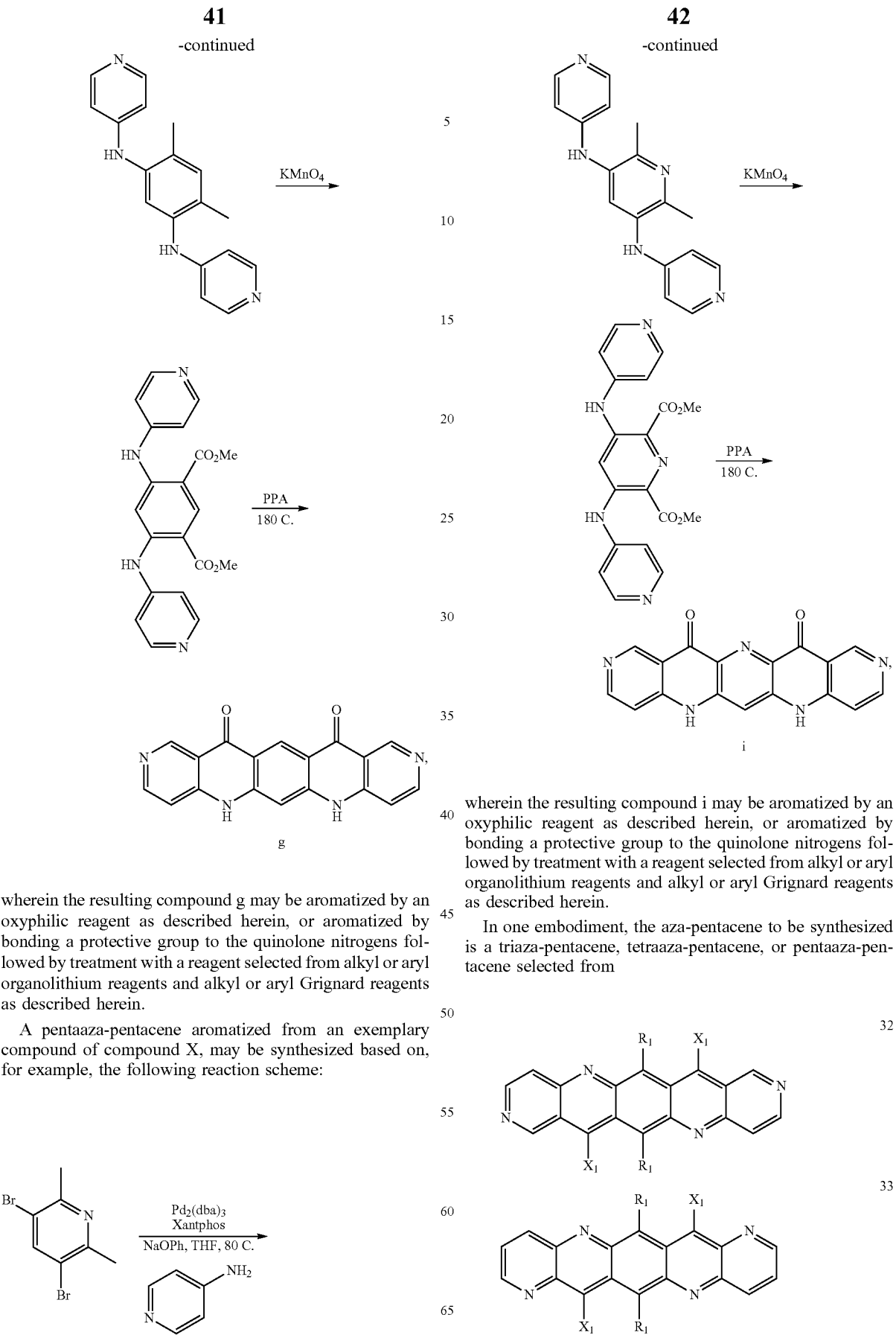

wherein the resulting compound g may be aromatized by an oxyphilic reagent as described herein, or aromatized by bonding a protective group to the quinolone nitrogens followed by treatment with a reagent selected from alkyl or aryl organolithium reagents and alkyl or aryl Grignard reagents as described herein.

A pentaaza-pentacene aromatized from an exemplary compound of compound X, may be synthesized based on, for example, the following reaction scheme:

wherein the resulting compound i may be aromatized by an oxyphilic reagent as described herein, or aromatized by bonding a protective group to the quinolone nitrogens followed by treatment with a reagent selected from alkyl or aryl organolithium reagents and alkyl or aryl Grignard reagents as described herein.

In one embodiment, the aza-pentacene to be synthesized is a triaza-pentacene, tetraaza-pentacene, or pentaaza-pentacene selected from 34
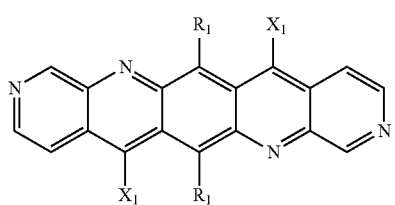
35
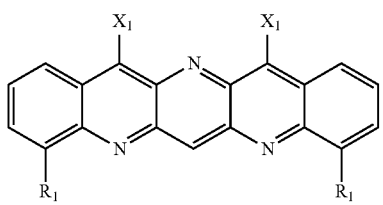
36
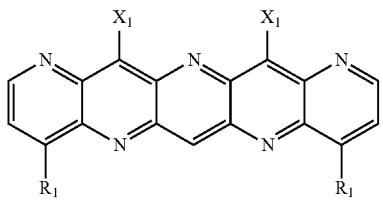
37
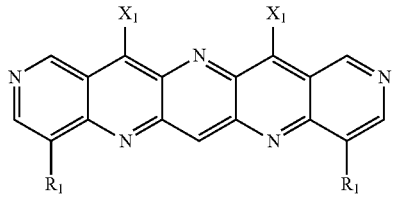
40
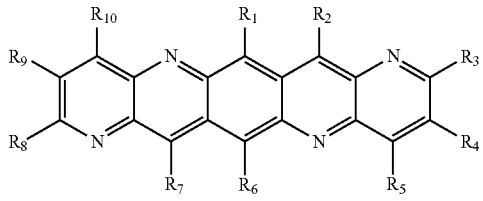
41
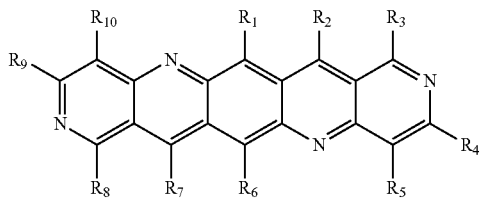
42
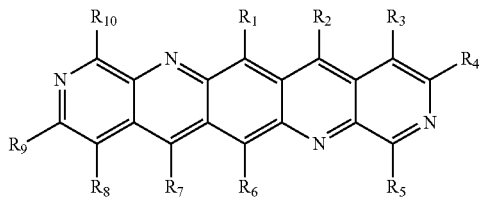
43
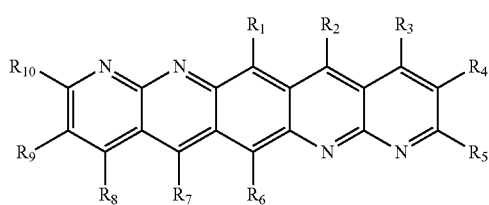
44
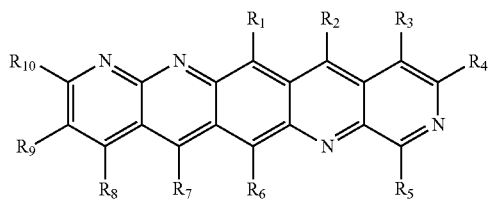
45
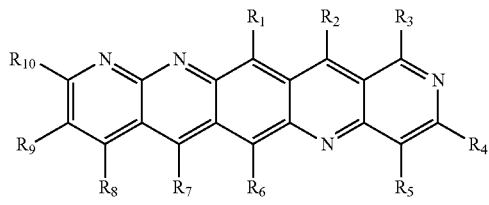
46
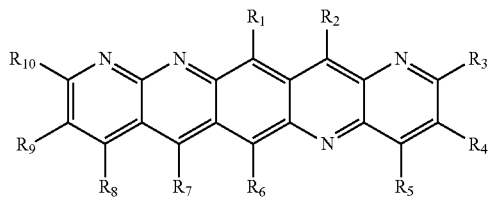
47
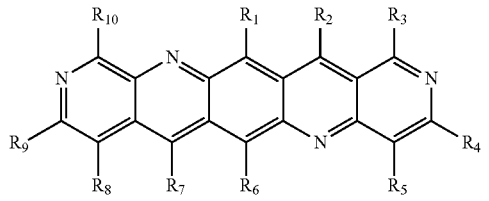
48
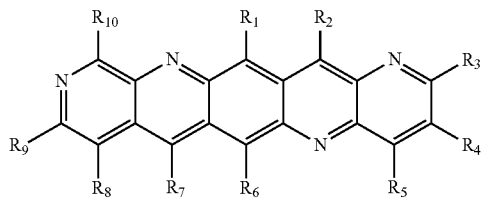
49
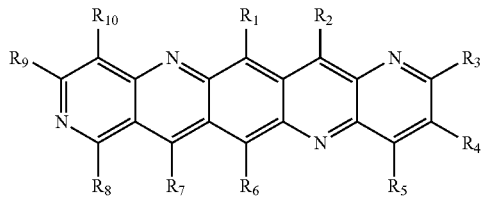

50
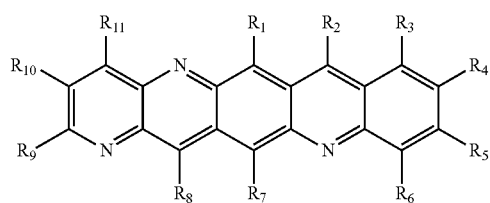
51
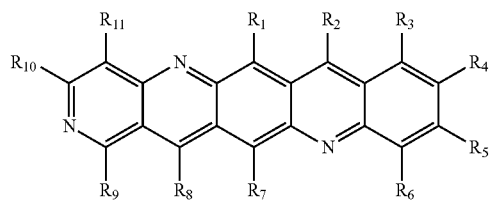
52
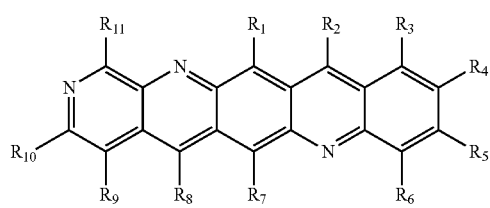
53
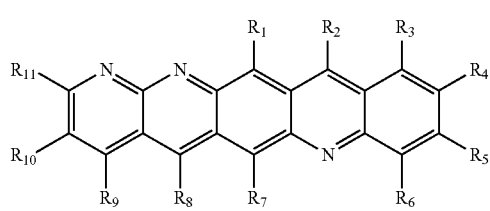
54
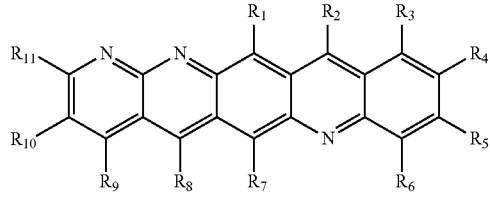
55
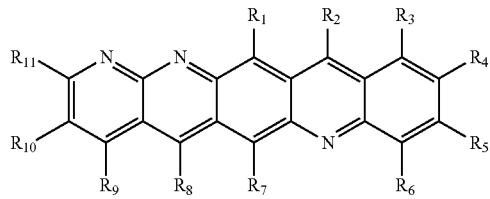
56
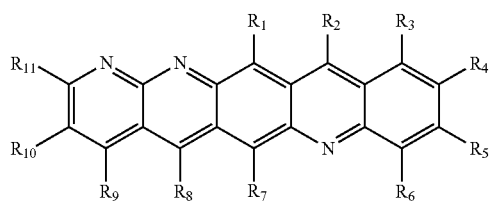
57
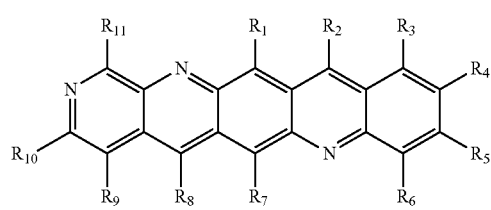
58
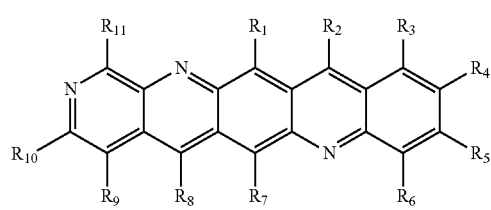
59
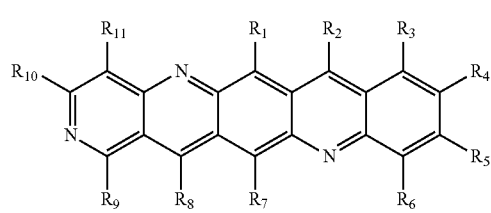
60
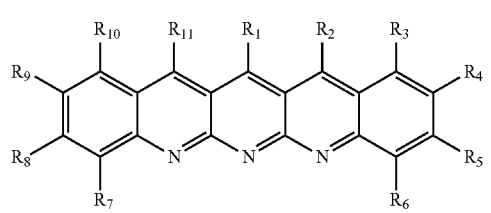
61
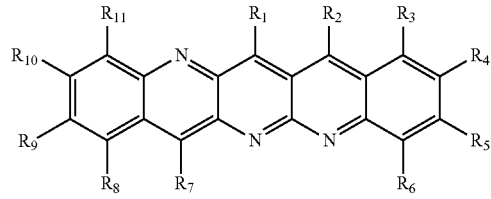
62
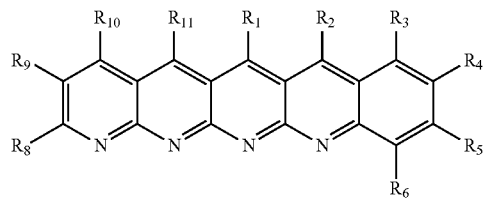
63
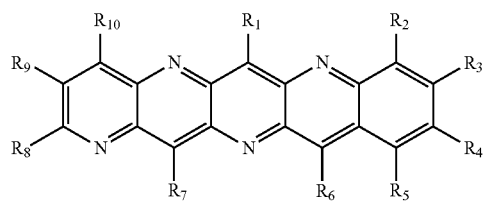

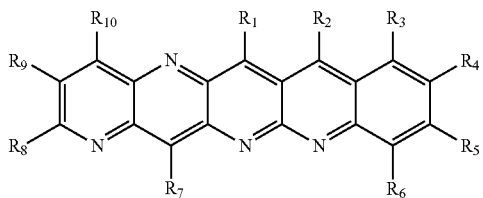
64

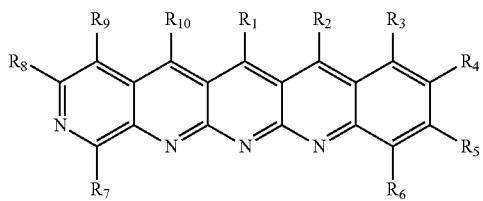
65

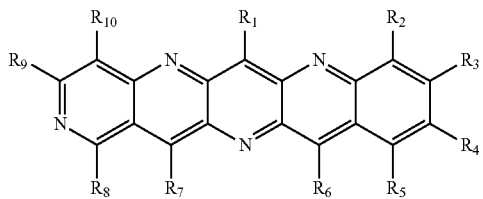
66

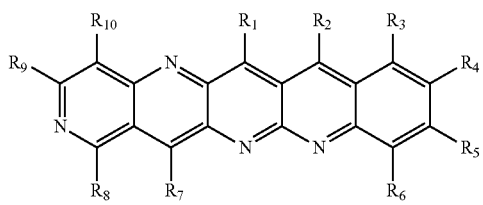
67

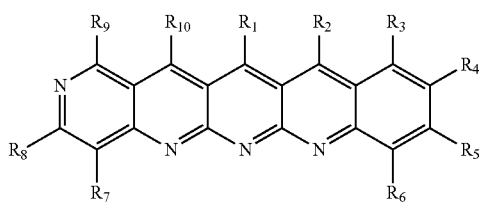
68

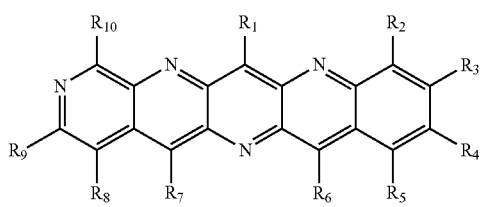
69

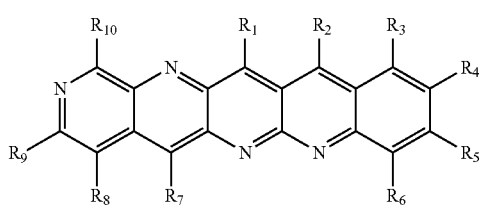
70

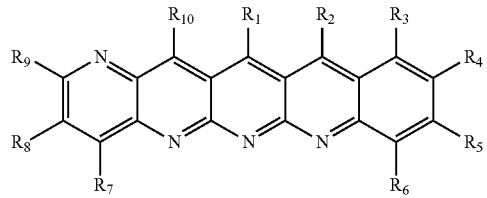
71

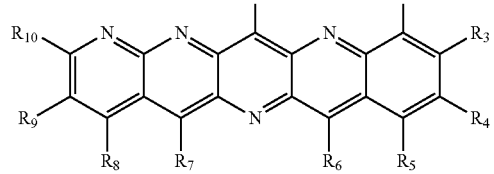
72

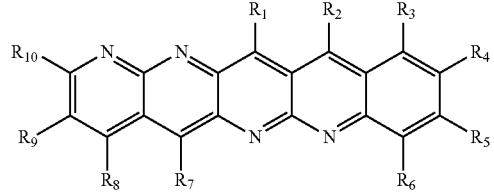
73 wherein $X_1$ and $R_n$ are independently selected from saturated carbocyclic, saturated heterocyclic, unsaturated carbocyclic, and unsaturated heterocyclic rings with adjacent $R_n$, a H, an aryl, a halide, a pseudohalide, an alkyl, and an electron acceptor.

The reaction schemes provided herein serve as examples only and are not meant to limit the invention in any way. One of ordinary skill in the art would understand that the chemistry disclosed herein allows for a variety of aza-acenes, such as aza-tetracenes and aza-pentacenes, to be envisioned. For example, reaction materials may be modified to vary the degree and position of aza-substitution, as well as to obtain desired substituents on the aza-acenes. The aza-acene compounds may be symmetric or asymmetric with a varying number of quinolone residues present in the precursor compound for later aromatization. This would allow one of ordinary skill in the art to place nitrogen at virtually any position 1-12 in tetracene or 1-14 in pentacene.

The aza-acene compounds contemplated by the present invention may be used as n-type materials in organic electronics. In one embodiment, there is disclosed an organic photosensitive optoelectronic device comprising at least one aza-acene. In some embodiments, the at least one aza-acene is selected from aza-tetracenes and aza-pentacenes.

In some embodiments, the at least one aza-acene compound is an aza-tetracene selected from diaza-tetracenes, triaza-tetracenes, and tetraaza-tetracenes.

In some embodiments, the at least one aza-acene compound is an aza-tetracene having a general formula selected from

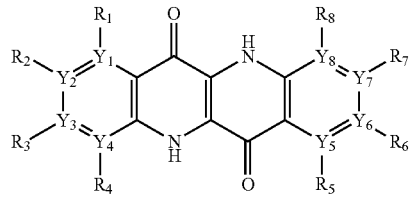
I

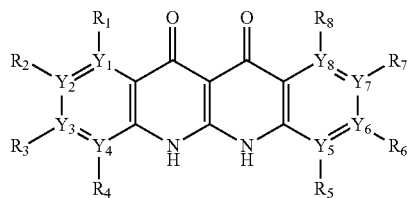

II

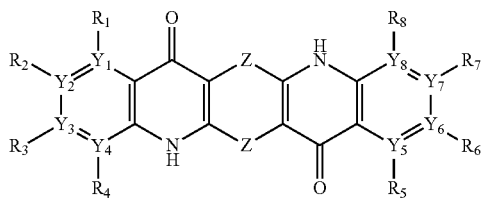

VII

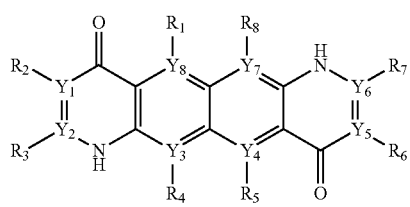

III

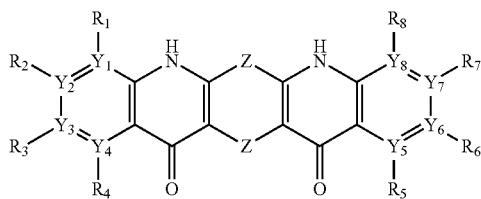

VIII

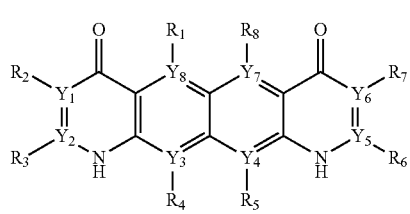

IV

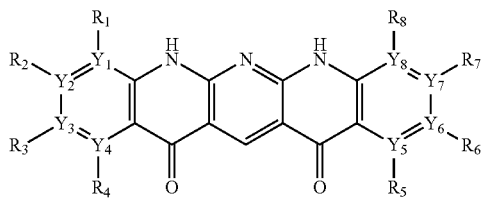

IX

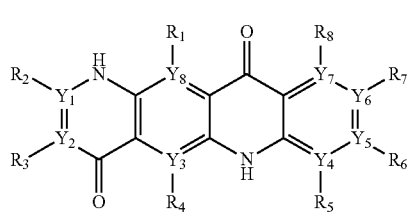

V

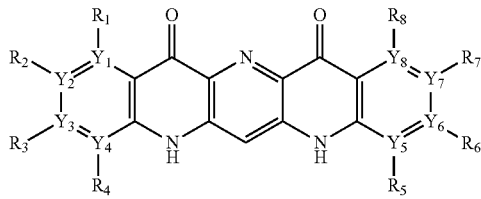

X

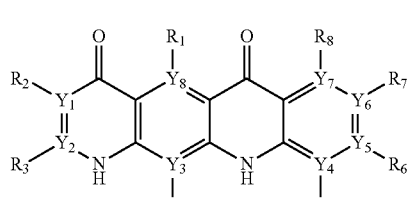

VI

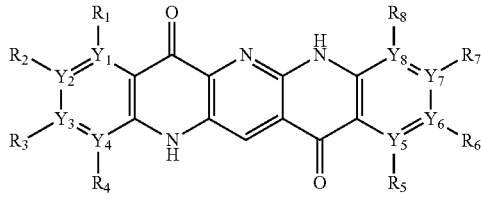

XI

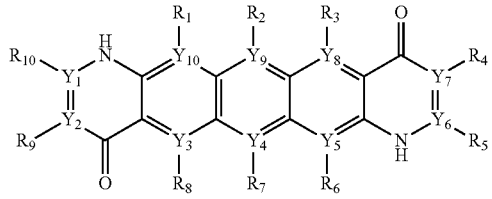

XII wherein $Y_n$ are independently selected from C and N, and $R_n$ are independently selected from saturated carbocyclic, saturated heterocyclic, unsaturated carbocyclic, and unsaturated heterocyclic rings with adjacent $R_n$, a H, an aryl, a halide, a pseudohalide, an alkyl, and an electron acceptor with the proviso that any of $R_n$ is H when the Y to which it is bonded is N.

In some embodiments, the at least one aza-acene compound is an aza-pentacene selected from diaza-pentacenes, triaza-pentacenes, tetraaza-pentances, and pentaaza-pentacenes.

In some embodiments, the at least one aza-acene compound is an aza-pentacene having a general formula selected from

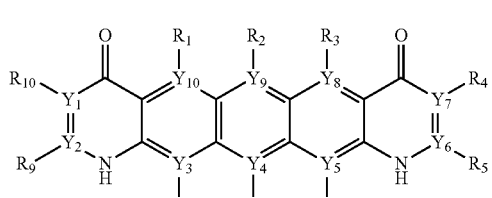

XIII

-continued

XIV
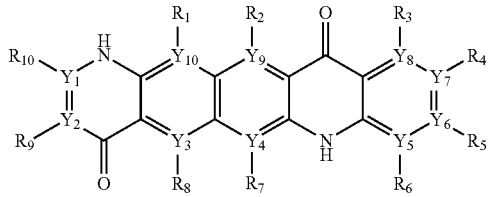

XV
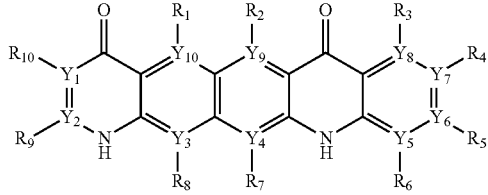

XVI
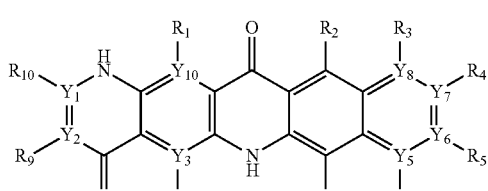

XVII
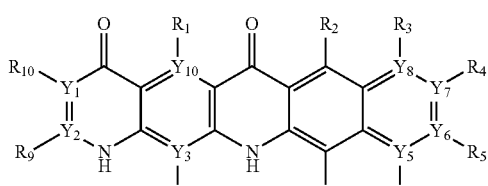

XVIII
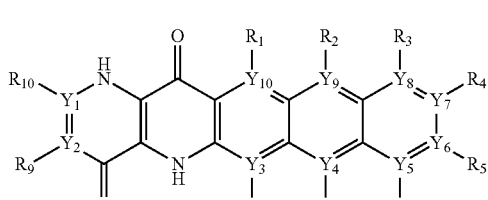

XIX
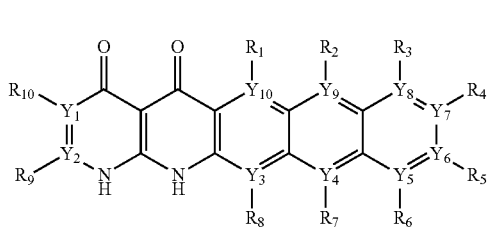

wherein $Y_n$ are independently selected from C and N, $R_n$ are independently selected from saturated carbocyclic, saturated heterocyclic, unsaturated carbocyclic, and unsaturated heterocyclic rings with adjacent $R_n$, a H, an aryl, a halide, a pseudohalide, an alkyl, and an electron acceptor with the proviso that any of $R_n$ is H when the Y to which it is bonded is N, and Z is selected from CH and $CH_2$.

In some embodiments, the organic photosensitive optoelectronic device comprises at least one donor-acceptor heterojunction. The donor-acceptor heterojunction may be formed at an interface of at least one donor material and at least one acceptor material. In some embodiments, the at least one acceptor material comprises the at least one aza-acene compound. In some embodiments, the aza-acene compound is selected from aza-tetracenes and aza-pentacenes. In some embodiments, the aza-tetracene is selected from diaza-tetracenes, triaza-tetracenes, and tetraaza-tetracenes. In some embodiments, the aza-pentacene is selected from diaza-pentacene, triaza-pentacene, tetraaza-pentacene, and pentaaza-pentacene.

In some embodiments, the diaza-tetracene is selected from 4,10-diphenyl-3,9-diaza-tetracene (DPDAT), 4,8,10,14-tetraphenyl-3,9-diaza-tetracene (TPDAT), 4,10-dichloro-3,9-diaza-tetracene (DCDAT), 8,14-diphenyl-4,10-dichloro-3,9-diaza-tetracene (DPDCDAT), 8,14-diphenyl-4,10-dicyano-3,9-diaza-tetracene (DPDCNDAT), and 4,10-dicyano-3,9-diaza-tetracene (DCNDAT).

In some embodiments, the at least one donor material is chosen from squarine (SQ), boron subphthalocyanonine chloride (SubPc), copper phthalocyanine (CuPc), chloroaluminum phthalocyanine (ClAlPc), poly(3-hexylthiophene) (P3HT), tin phthalocyanine (SnPc), diindenoperylene (DIP), and combinations thereof.

In some embodiments, the diaza-tetracene is DPDCNDAT and the at least one donor material is SubPc.

In one embodiment, the organic photosensitive optoelectronic device has the structure ITO/SubPc/DPDCNDAT/BCP/Al.

The organic photosensitive devices of the present invention may be structured in various configurations with varying material combinations. U.S. Patent Publication No. 2012/0235125 is hereby incorporated by reference for its disclosure of organic photovoltaic device structures and materials.

In some embodiments, the organic photosensitive optoelectronic device is a solar cell.

In some embodiments, the organic photosensitive optoelectronic device is a photodetector.

As used herein, the term "alkyl" means a straight-chain or branched saturated hydrocarbyl group. Examples of alkyl groups include methyl, ethyl, n-propyl, isopropyl, n-butyl, sec-butyl, isobutyl, tert-butyl, n-pentyl and n-hexyl.

As used herein, the term "aryl" means an aromatic hydrocarbyl group. The aryl group may be monocyclic or multicyclic. Examples of aryl groups include phenyl and naphthyl groups.

As used herein, the term "electron acceptor" means functional groups that have vacant pi-symmetry molecular orbitals, which are within 1-2 eV of the HOMO of the molecule they are appended to. These materials interact with the molecule by accepting electron density and thus lowering the energy of the molecule's HOMO. Common electron acceptors include, for example, nitro, cyano, formyl, phenyl, vinyl immine, tricyano-vinyl, fluoroalkyl, pyridinium, carboxyl, and ester groups.

EXAMPLES

Figure 1:
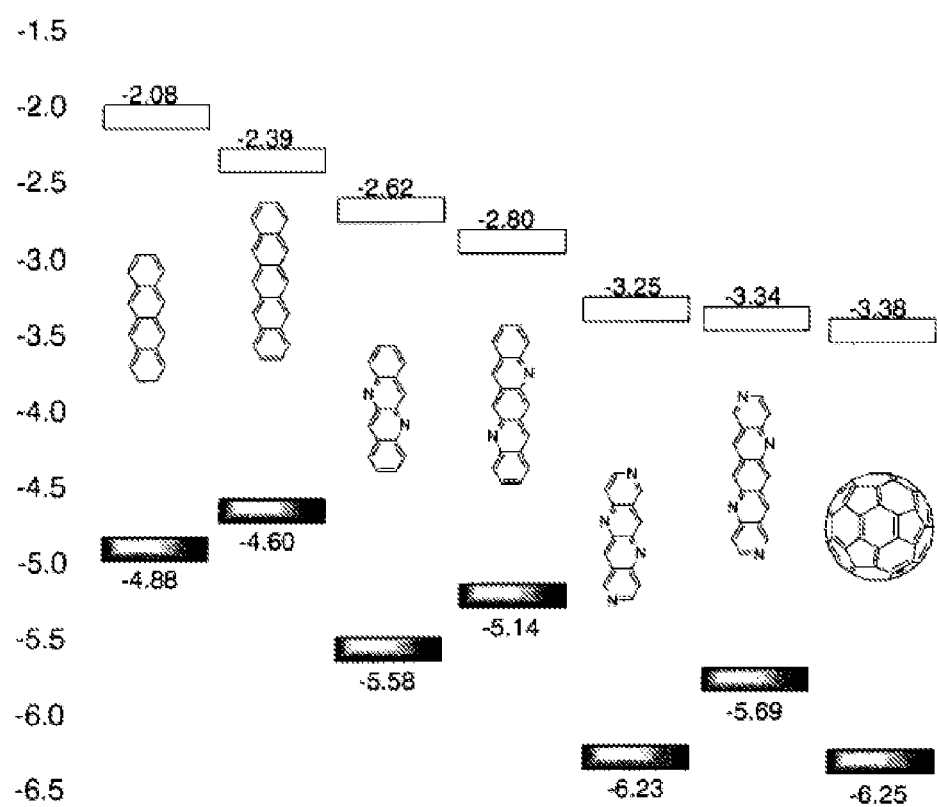
FIG. 1 depicts the systematic lowering of HOMO and LUMO energy levels calculated at B3LYP/6-31G* for aza-tetracenes and aza-pentacenes.
Figure 2:
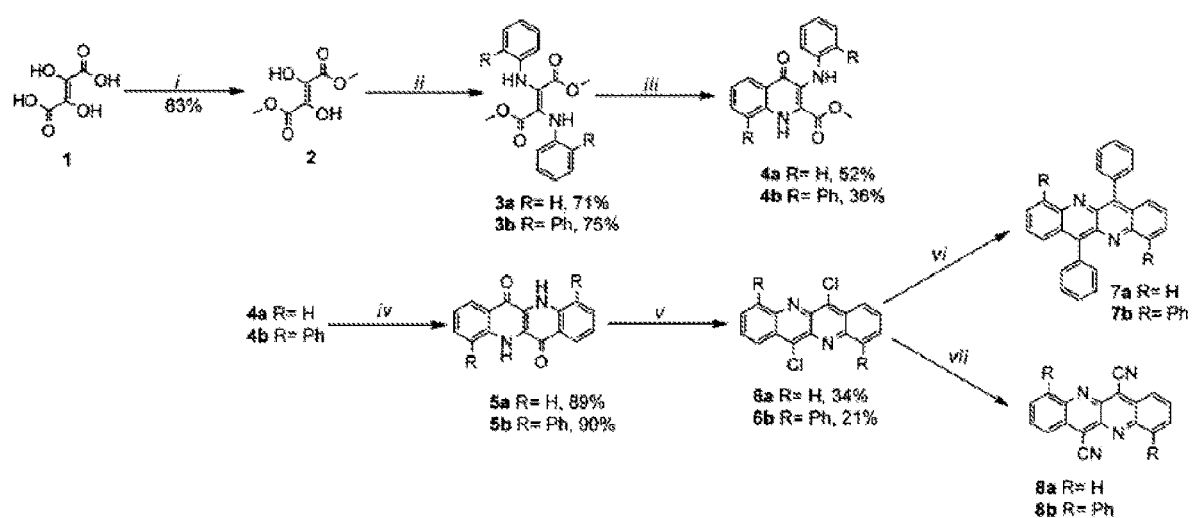
FIG. 2 shows an exemplary synthetic scheme for the synthesis of a 3,9-diaza-tetracene.

FIG. 2 provides an example of a synthesis for 3,9-diaza-tetracenes in accordance with the present invention. Epindolidiones (5a-b) were prepared starting from commercially available dihydroxy fumaric acid. Compound 1 was treated with thionyl chloride in dry methanol to afford the methyl ester 2 in 74% yield. The dimethyl bis(arylamino)maleates (3a-b) were obtained in good yield by refluxing 2 in methanol with a catalytic amount of HCl in the presence of an aryl aniline. Maleates (3a-b) were then subjected to refluxing Dowtherm A to afford the 2-methoxycarbonyl-3-arylamino-4-quinolones (4a-b). Heating 4a-b in polyphosphoric acid for 2 hours afforded epindolidiones (5a-b) in excellent yield. Treatment of epindolidione (5a-b) in neat phosphorous oxychloride in the presence of $K_2CO_3$ gave the 4,10-dichloro-3,9-diaza-tetracenes (6a-b) in modest yields. Compound 6a was subjected to a variety of Suzuki coupling conditions all of which failed or gave yields <10% of compound 7a. Under Kumada conditions using PEPPSI-IPr as the palladium source, compounds 7a-b were prepared in excellent yields. Cyanation of 6a-b with a catalytic amount of sodium p-$SO_2$Ph with KCN in hot DMF afforded 8a-b in low yields.

As an additional example of the synthetic scheme shown in FIG. 2, the individual reactions are further explained as follows:

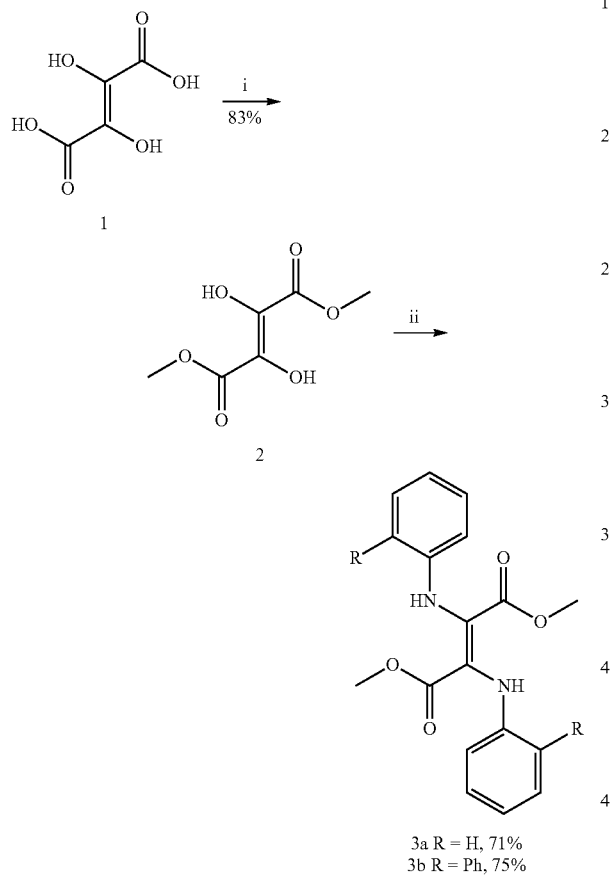

Dimethyl dihydroxyfumarate (2) was prepared by stirring a solution of 1 (25.00 g, 16.9 mmol) with 50 g of $MgSO_4$ in 200 mL of dry MeOH and cooling to 0° C. The mixture was purged with dry HCl for 4 hours. The ice bath was removed and the reaction stirred for 2 hours at room temperature. The mixture was left at room temperature overnight undisturbed. A white precipitate formed and was collected by vacuum filtration and washed with cold MeOH. The white solid was suspended in ice cold $H_2O$ (400 mL) and vigorously stirred then immediately collected by filtration, washed with cold $H_2O$ and MeOH. The material was air dried overnight to give 24.6 g (83%) of dimethyl dihydroxyfumarate (2). Dimethyl 2,3-bis(phenylamino)fumarate (3a) was prepared by stirring a solution of 2 (14.3 g, 81.2 mmol) and aniline (22.7 g, 243.7 mmol) in 200 mL of dry MeOH under a $N_2$ atmosphere. The reaction mixture was heated to reflux overnight after the addition of 3 mL of Concentrated HCl. A yellow precipitate formed and was filtered off after cooling the reaction to 0° C. The precipitate was washed thoroughly with cold MeOH and hexanes and was allowed to air dry to give 18.72 g (71%) of dimethyl 2,3-bis(phenylamino)fumarate (3a). Dimethyl 2,3-bis([1,1'-biphenyl]-2-ylamino)fumarate (3b) was prepared by stirring a solution of 2 (9.4 g, 53.4 mmol) and 2-aminobiphenyl (20.0 g, 118.2 mmol) in 100 mL of dry MeOH under a $N_2$ atmosphere. The reaction mixture was heated to reflux overnight after the addition of 1.5 mL of Concentrated HCl. A bright yellow precipitate was collected by filtration, washed with MeOH and hexanes to give 19.03 g (75%) of dimethyl 2,3-bis([1,1'-biphenyl]-2-ylamino)fumarate (3b).

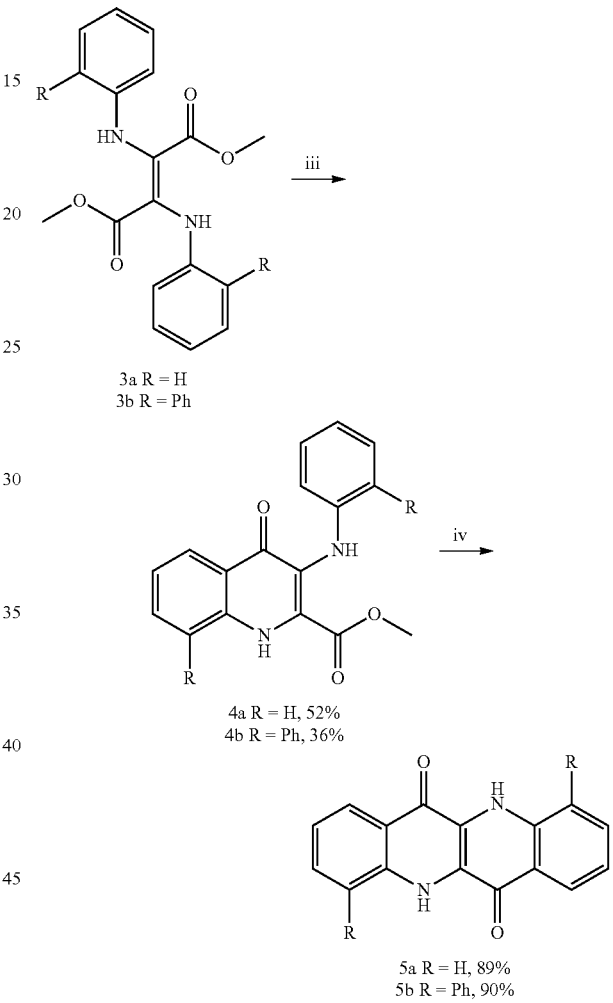

2-Methoxycarbonyl-3-arylamino-4-quinolone (4a) was prepared by heating a solution of 3a (12.91 g, 39.5 mmol) in Dowtherm A (80 mL) to 120° C. and adding the solution dropwise to 100 mL of refluxing Dowtherm A under $N_2$ atmosphere. The reaction was further refluxed for 1 hour after the addition, cooled to room temperature, and left overnight. A yellow precipitate was collected by filtration and washed repeatedly with hexanes. The material was air dried to yield 5.03 g (43%) of 2-methoxycarbonyl-3-arylamino-4-quinolone (4a). 2-Methoxycarbonyl-3-arylamino quinolone (4b) was prepared by heating a solution of 3b (14.3 g, 29.8 mmol) in Dowtherm A (80 mL) to 120° C. and adding the solution dropwise to 100 mL of refluxing Dowtherm A under $N_2$ atmosphere. The reaction was further refluxed for 1 hour after the addition, cooled to room temperature, and left overnight. A red precipitate was collected by filtration and washed repeatedly with hexanes. The material was air dried to yield 8.25 g (62%) of 2-methoxycarbonyl-3-arylamino-4-quinolone (4b). Epindolidione (5a) was prepared by charging a 250 mL round bottom flask with ~100 mL of PPA followed by 9.5 g of 4a under a $N_2$ atmosphere. The mixture was heated to 150° C. for 2 hours. The reaction was cooled to ~90° C., slowly adding water to the reaction mixture until the vigorous hydrolysis reaction ceased. The mixture was then poured into 300 mL of water and vigorously stirred. The yellow precipitate was collected by filtration and then suspended in 400 mL of THF and vigorously stirred. The bright yellow precipitate was collected by filtration and washed with MeOH to yield 7.55 g (89%) of epindolidione (5a). 4,10-Diphenyl epindolidione (5b) was prepared by charging a 100 mL schlenk flask with ~60 mL of PPA with 4.7 g of 4b under a $N_2$ atmosphere. The mixture was heated to 150° C. for 2 hours. The reaction was cooled to ~90° C., slowly adding water to the reaction mixture until the vigorous hydrolysis reaction ceased. The mixture was then poured into 300 mL of water and vigorminutes. The reaction was heated to 90° C. overnight. The reaction was cooled to room temperature and $POCl_3$ was removed by vacuum distillation. The crude material was then added to 500 mL of aqueous 10% $K_2CO_3$ and vigorously stirred. The precipitate was collected and loaded on silica gel and eluted with $CHCl_3$ to yield 1.44 g (54%) of 4,10-dichloro-3,9-diazatetracene (6a). 2,8-Diphenyl-4,10-dichloro-3,9-diazatetracene (6b) was prepared by stirring a solution of 5b (5 g, 12.1 mmol) in $POCl_3$ (250 mL) with $K_2CO_3$ (15.0 g, 108.5 mmol) and purging with $N_2$ for 20 minutes. The reaction was heated to 90° C. overnight. The reaction was cooled to room temperature and $POCl_3$ was removed by vacuum distillation. The crude material was then added to 500 mL of aqueous 10% $K_2CO_3$ and vigorously stirred. The precipitate was collected and loaded on silica gel and eluted with $CHCl_3$ to yield 2.39 g (44%) of 2,8-diphenyl-4,10-dichloro-3,9-diazatetracene (6b).

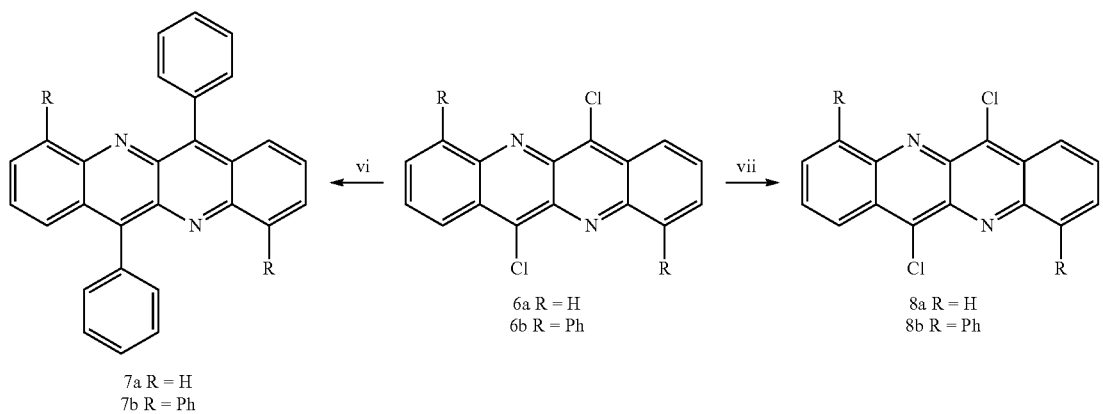

7a R = H
7b R = Ph

6a R = H
6b R = Ph

8a R = H
8b R = Ph ously stirred. The precipitate was collected and suspended in 300 mL of THF and vigorously stirred. A bright yellow precipitate was collected by filtration and washed with hexanes to yield 3.93 g (90%) of 4,10-diphenyl epindolidione (5b).

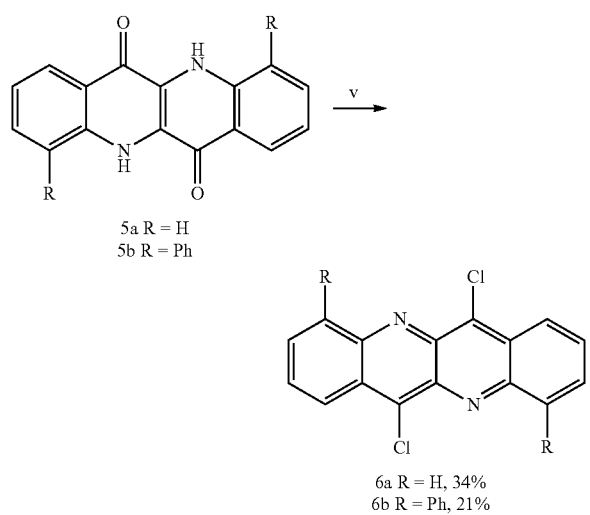

5a R = H
5b R = Ph

6a R = H, 34%
6b R = Ph, 21%

4,10-Dichloro-3,9-diazatetracene (6a) was prepared by stirring a solution of 5a (2.35 g, 8.96 mmol) in $POCl_3$ (130 mL) with $K_2CO_3$ (7.00 g, 50.6 mmol) and purging with $N_2$ for 20

4,10-Diphenyl-3,9-diazatetracene (7a) was prepared by charging an oven dried 100 mL schlenk flask with 6a (400 mg, 1.34 mmol) and 10 mol % of PEPPSI-IPr (91 mg) in dry dioxane (60 mL) and purging with $N_2$ for 20 minutes. 3.0 M phenyl magnesium bromide (2.67 mL, 8.02 mmol) was then added dropwise to the reaction mixture. After the addition, the reaction was heated to 70° C. The reaction was cooled to room temperature and diluted with ethyl acetate (30 mL) and stirred. The solvent was removed and the crude material was purified by column chromatography and then recrystallized from toluene to yield 448 mg (88%) of 4,10-diphenyl-3,9-diazatetracene (7a). 2,4,8,10-tetraphenyl-3,9-diazatetracene (7b) was prepared by charging an oven dried 100 mL schlenk flask with 6b (603 mg, 1.34 mmol) and 10 mol % of PEPPSI-IPr (91 mg) in dry dioxane (60 mL) and purging with $N_2$ for 20 minutes. 3.0 M phenyl magnesium bromide (2.67 mL, 8.02 mmol) was then added dropwise to the reaction mixture. After the addition, the reaction was heated to 70° C. The reaction was cooled to room temperature and diluted with ethyl acetate (30 mL) and stirred. The solvent was removed and the crude material was purified by column chromatography and then recrystallized from ethyl acetate and hexanes to yield 394 mg (55%) of 2,4,8,10-tetraphenyl-3,9-diazatetracene (7b). 4,10-Dicyano-3,9-diazatetracene (8a) was prepared by stirring in an oven dried 250 mL schlenk flask 6a (500 mg, 1.67 mmol), 18-crown-6 (133 mg), potassium cyanide (655 mg, 10.06 mmol) and PEPPSI-IPr (170 mg, 15 mol %) in dry DMF (150 mL) and purging with $N_2$ for 20 minutes. The reaction was then heated to 90° C. overnight in an oil bath. The reaction was cooled to room temperature and then DMF was removed by vacuum distillation. The crude material was loaded on silica and purified by column chromatography eluting with DCM: Hexane (80:20) to yield 90 mg (20%) of 4,10-dicyano-3,9-diazatetracene (8a). 2,8-Diphenyl-4,10-dicyano-3,9-diazatetracene (8b) was prepared by stirring in an oven dried 250 mL schlenk flask 6b (200 mg, 0.44 mmol), 18-crown-6 (20 mg), potassium cyanide (165 mg, 2.53 mmol) and PEPPSI-IPr (45 mg, 15 mol %) in dry DMF (60 mL) and purging with $N_2$ for 20 minutes. The reaction was then heated to 90° C. overnight in an oil bath. The reaction was cooled to room temperature and then DMF was removed by vacuum distillation. The crude material was loaded on silica and purified by column chromatography eluting with DCM:Hexane (80: 20) to yield 84 mg (44%) of 2,8-diphenyl-4,10-dicyano-3, 9-diazatetracene (8b).

Figure 3:
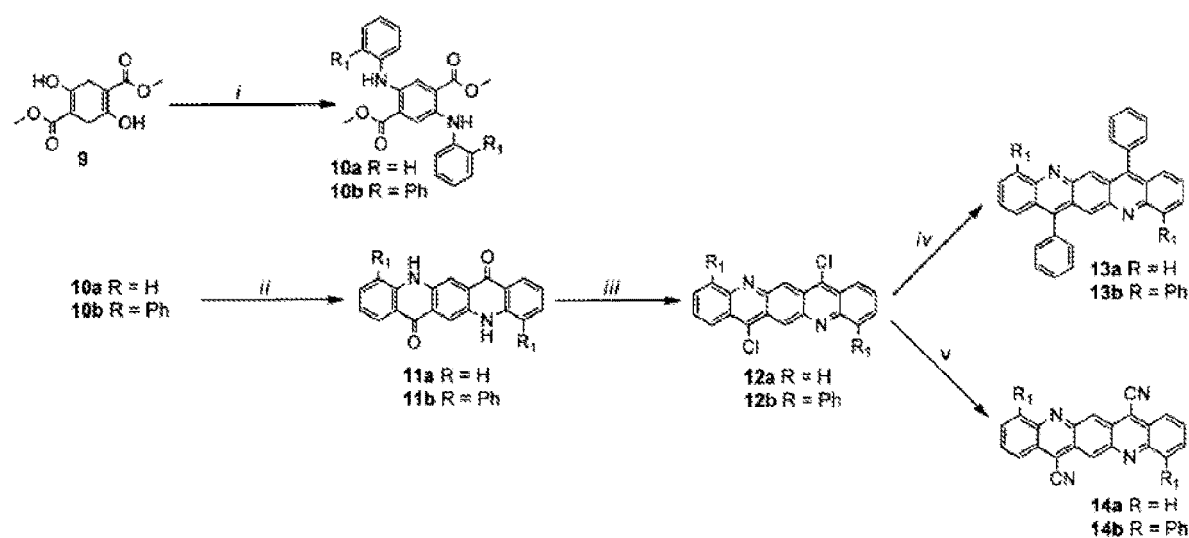
FIG. 3 shows an exemplary synthetic scheme for the synthesis of a 5,12-diaza-pentacene.
Figure 4:
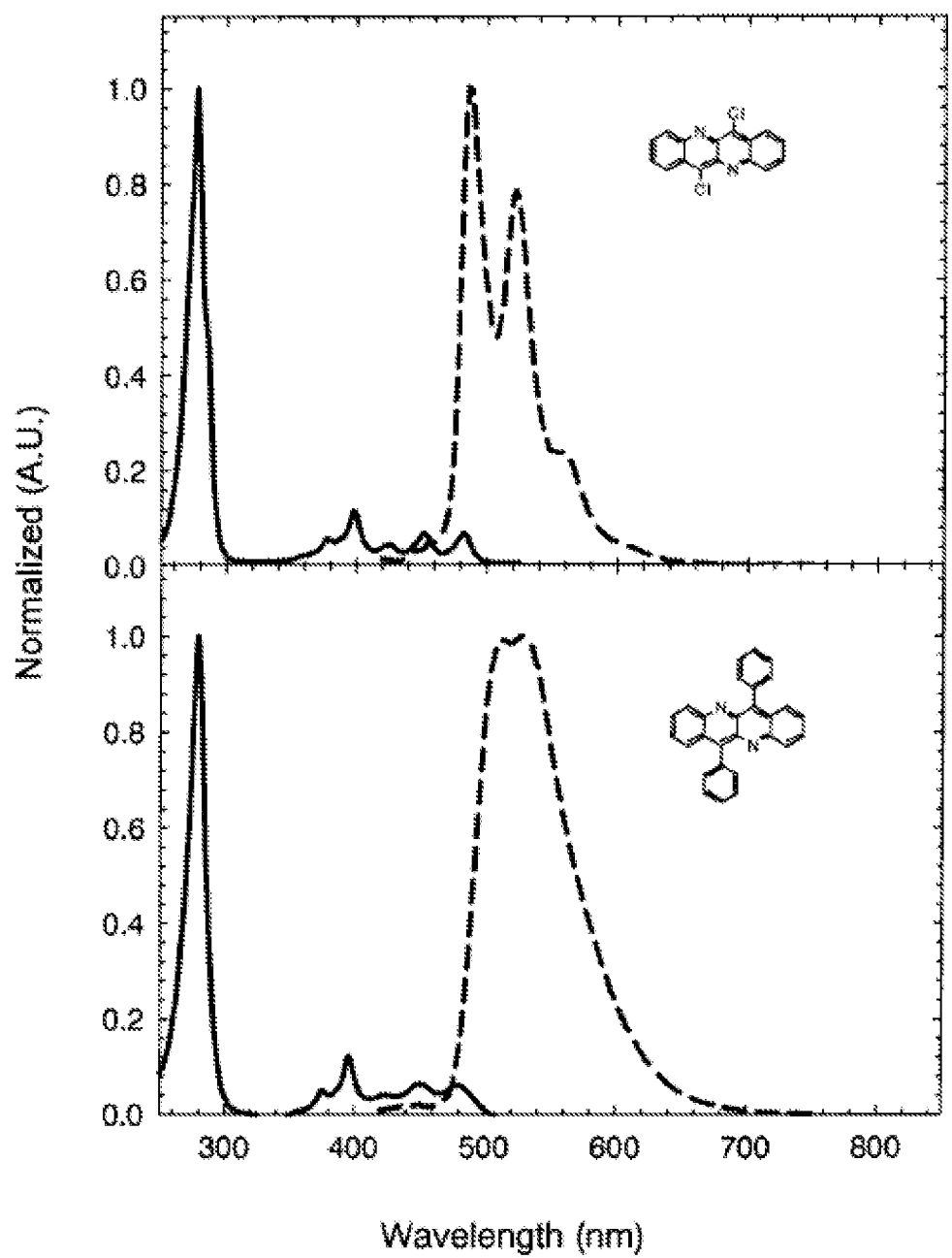
FIG. 4 shows the absorption spectrum of a 4,10-dichloro-3,9-diaza-tetracene and a 4,10-diphenyl-3,9-diaza-tetracene.
Figure 5:
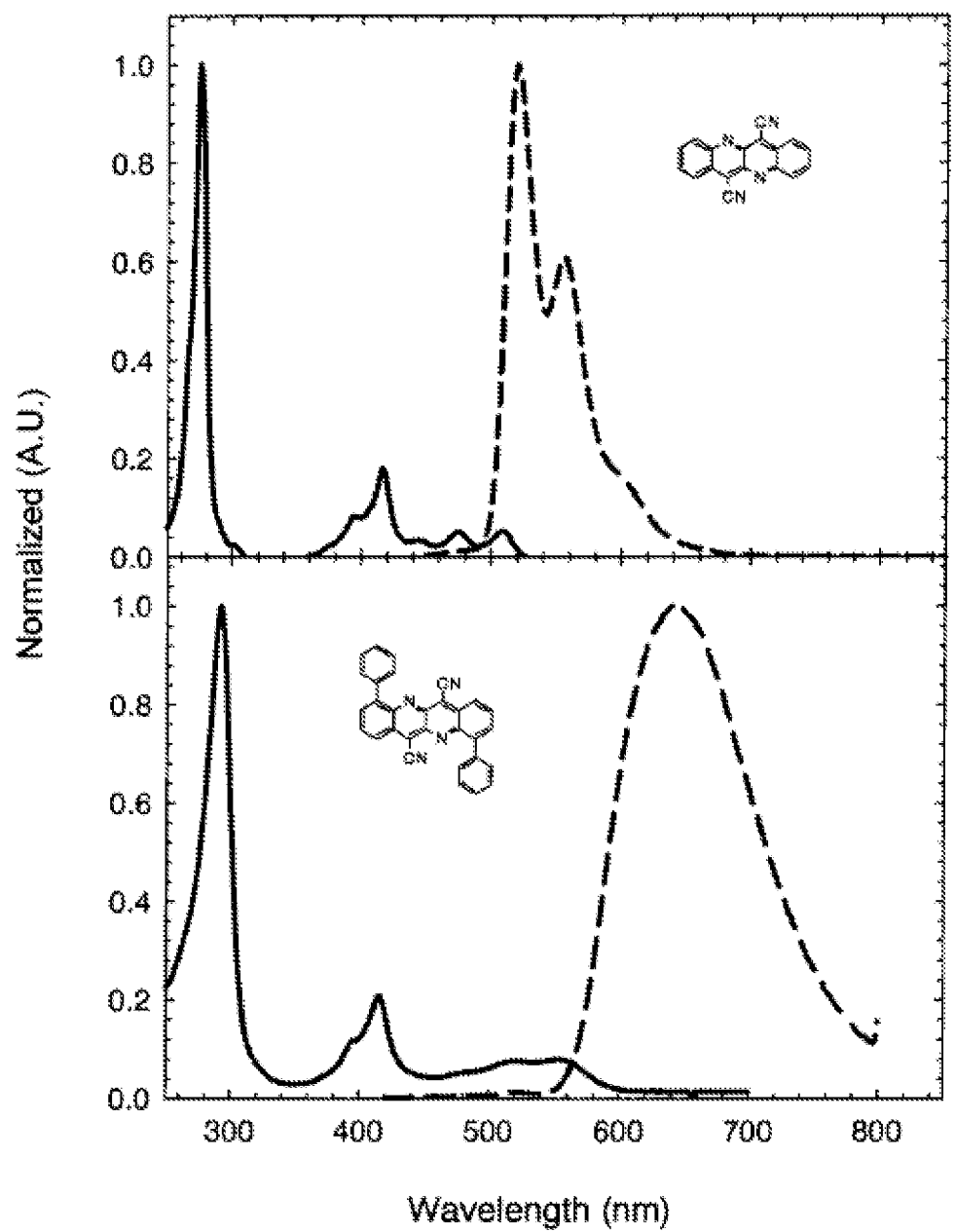
FIG. 5 shows the absorption spectrum of a 4,10-dicyano-3,9-diaza-tetracene and a 2,8-diphenyl-4,10-dicyano-3,9-diaza-tetracene.
Figure 6:
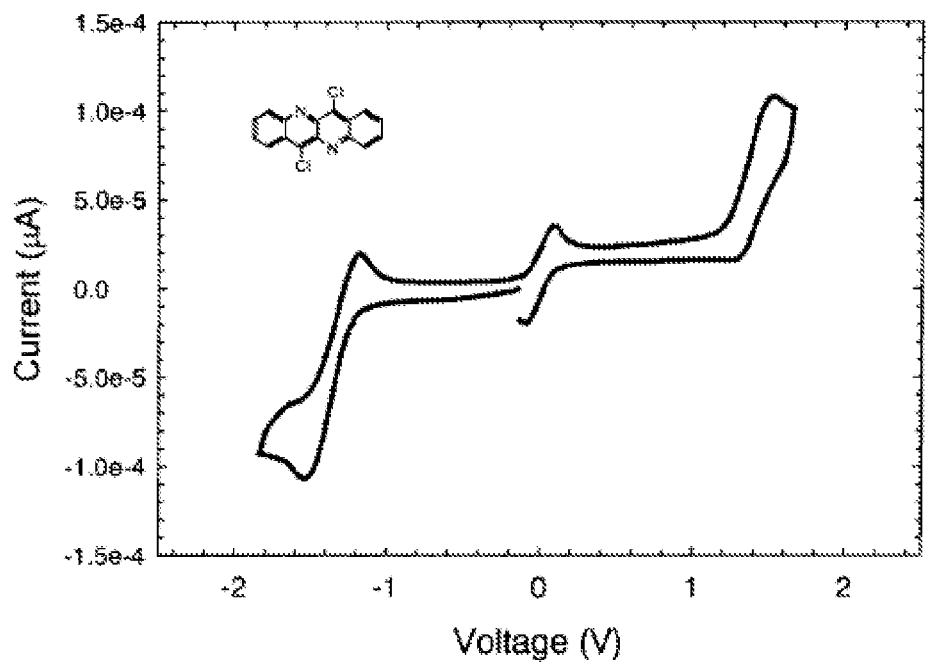
FIG. 6 shows cyclic voltammetry (CV) measurements for 4,10-dichloro-3,9-diaza-tetracene.
Figure 7:
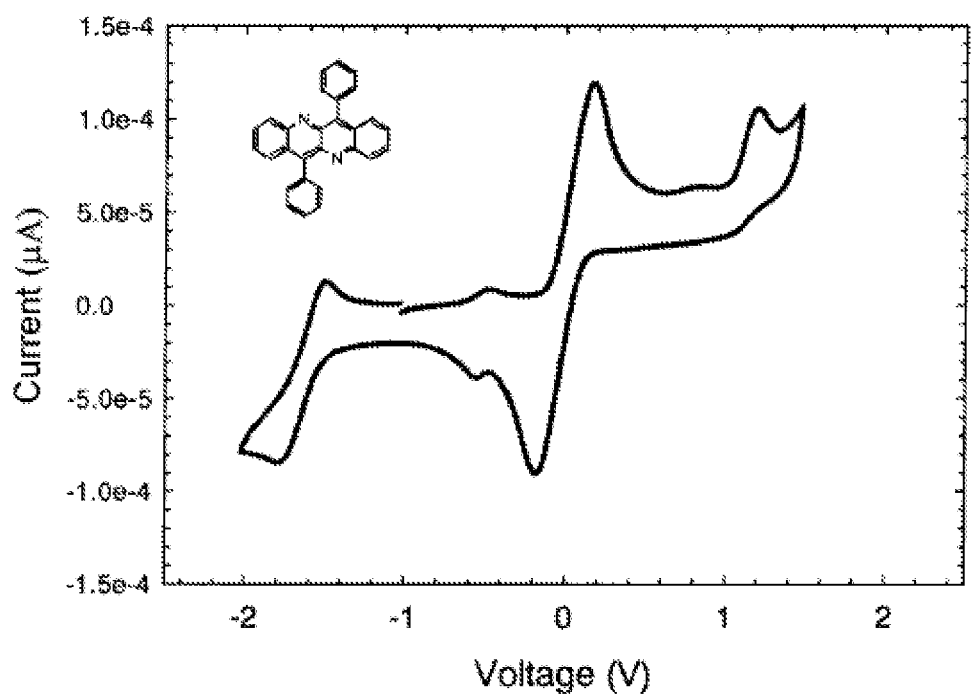
FIG. 7 shows CV measurements for 4,10-diphenyl-3,9-diaza-tetracene.
Figure 8:
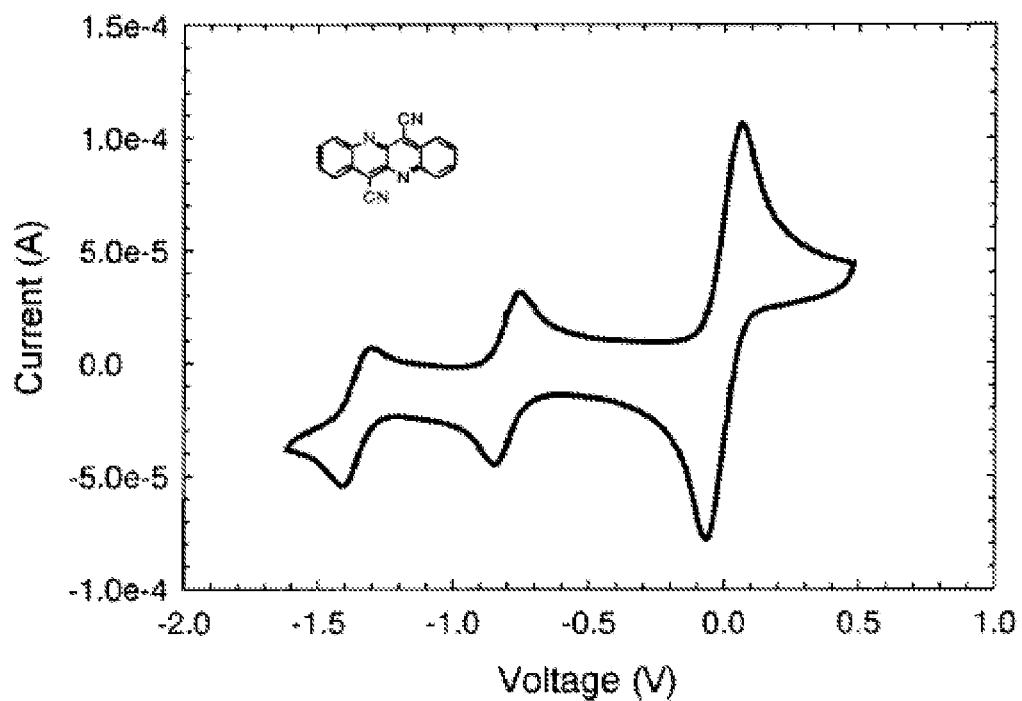
FIG. 8 shows CV measurements for 4,10-dicyano-3,9-diaza-tetracene.
Figure 9:
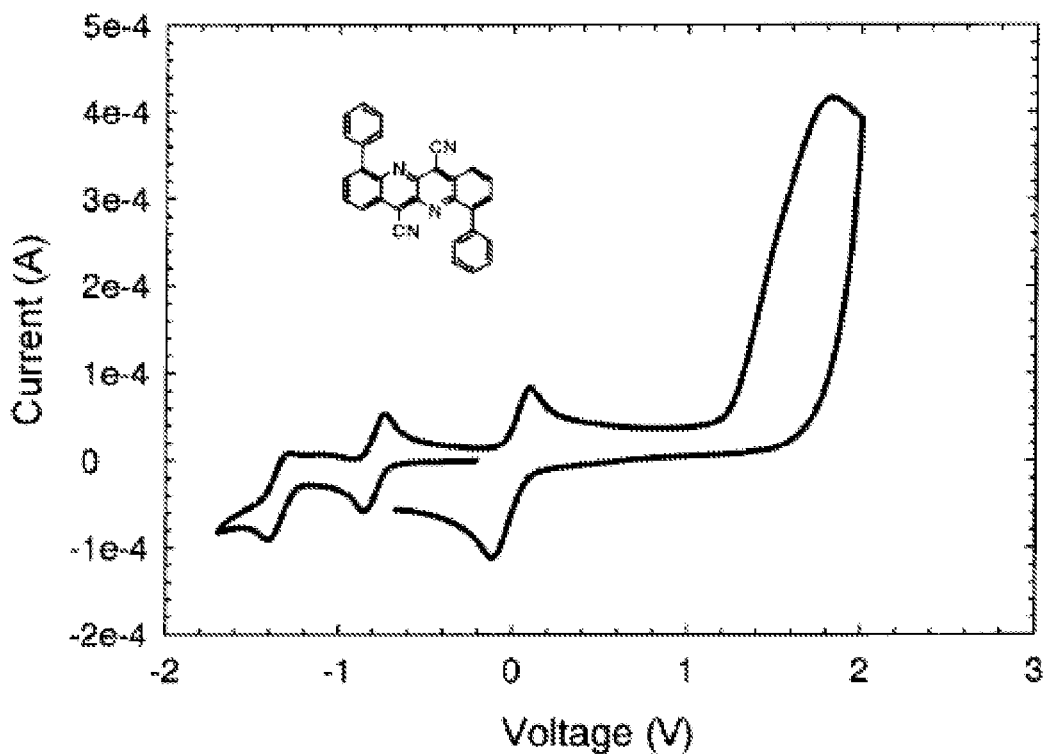
FIG. 9 shows CV measurements for 2,8-diphenyl-4,10-dicyano-3,9-diaza-tetracene.
Figure 10:
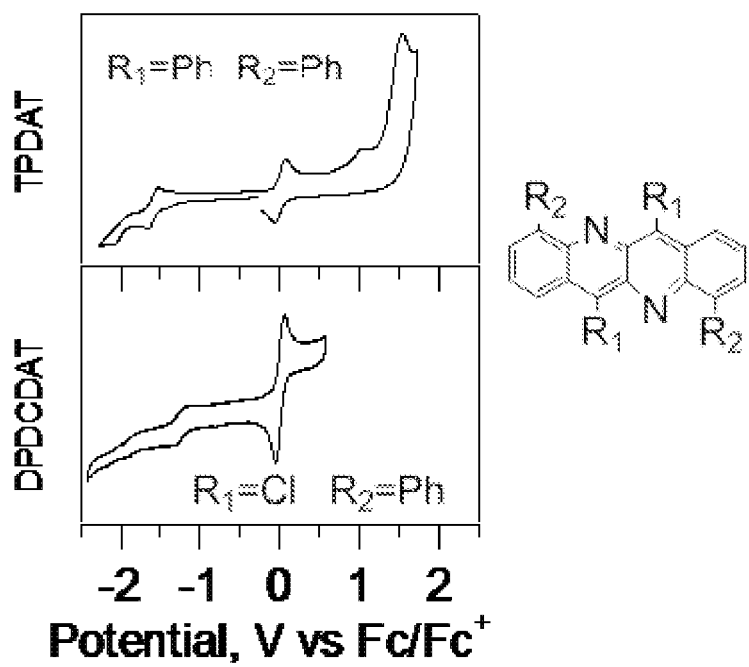
FIG. 10 shows CV measurements for additional aza-acene compounds.

FIG. 3 provides an example of a synthesis for 5,12-diazapentacenes in accordance with the present invention. Quinacridones (11a-b) were prepared starting from commercially available dimethyl succinylosuccinate (9). Compound 9 was refluxed in acetic acid open to atmosphere overnight in the presence of an aniline to give 10a-b in good yield. Cyclization of 10a-b in polyphosphoric acid gave quinacridones 11a-b in excellent yield. Treatment of 11a-b or the sodium salt of 11a-b in neat phosphorous oxychloride in the presence of $K_2CO_3$ afforded 7,14-dichloro-5,12-diazapentacenes (12a-b). Compounds 13(a-b) and compounds 14(a-b) were prepared following the same technique used to prepare 7(a-b) and 8(a-b) from 6(a-b).

FIGS. 6-10 show CV measurements for particular aza-acene compounds. All CV measurements were performed using a EG&G Potentiostat/Galvanostat model 283. All scans were recorded at a scan rate of 50 mV/s in dry and degassed DCM with 0.1 M tetra(n-butyl)ammonium hexafluorophosphate (Aldrich) as the supporting electrolyte. Ferocene/ferrocenium ($Fc/Fc^+$) redox couple was used as an internal standard. A glassy carbon rod, a platinum wire, and a silver wire were used as the working electrode, the counter electrode, and the pseudo reference electrode, respectively.

Figure 11:
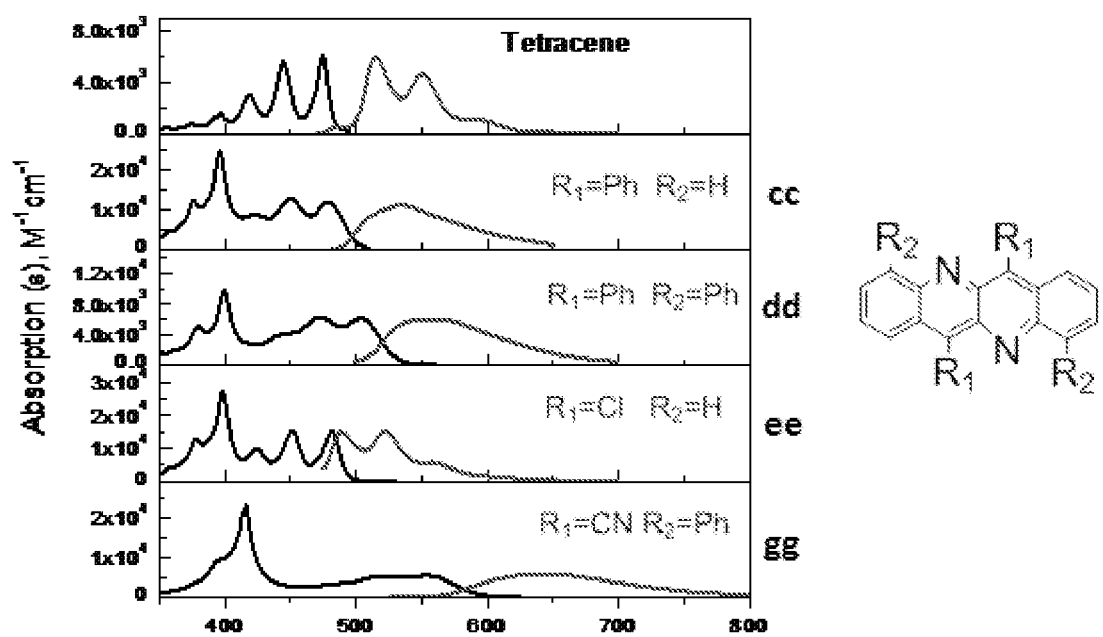
FIG. 11 shows absorption/emission spectra for particular diaza-tetracenes

FIG. 11 shows additional absorption/emission spectra for particular diaza-tetracenes.containing phenyl, chloro, or nitrile substituents and combinations thereof. Additionally, phenyl substituents were added at the 1 and 7 positions for select diaza-tetracenes. These substituents affect the frontier molecular orbital (FMO, i.e., HOMO, LUMO) energies, band gap, and crystal packing of the molecule. These material substitution patterns were chosen to minimize or eliminate their dipolar character, thereby preventing carrier trapping expected for disordered polar materials. The absorption of the diaza-tetracenes are red-shifted to tetracene with compound gg absorbing to 750 nm. With the exception of compound ee, the emission of the diaza-tetracenes are red-shifted relative to tetracene. Additionally, the structure seen in the emission diminishes with the addition of phenyl substituents at the 1 and 7 positions as evidenced in cc, dd, and gg.

FIG. 12 provides additional absorption and electrochemical properties of particular diaza-tetracenes. Electrochemical properties of the diaza-tetracenes were examined using cyclic voltammetry (CV). The primary reduction potentials of the diaza-tetracenes varied by 1V, from −1.77 V for cc to −0.78 V for hh. The LUMO energies of the diaza-tetracenes were calculated from the reduction potentials obtained through CV using previously published correlations. The optical energy gap, $E_g$, was taken as the intersection of the lowest energy transition and the fluorescence spectrum for the acenes, i.e. aa-hh, and the absorption edge for a thin film of $C_{60}$. The LUMO levels of gg and hh, are similar to that of $C_{60}$. The LUMO energies of ee, ff, gg, and hh suggest that they may be useful as acceptors in OPVs. The range of LUMO levels achieved here exhibit the wide FMO tunability that is available via this synthetic pathway.

X-Ray diffraction data were obtained for aza-tetracene thin films to determine their crystalline morphology. At both low (0.2 Å/s) and high (>20 Å/s) deposition rates in vacuum, the aza-tetracenes showed no diffraction peaks, suggesting an amorphous structure.

OPV devices were fabricated using copper phthalocyanine (CuPc), N,N'-Bis-(1-naphthalenyl)-N,N'-bis-phenyl-(1, 1'-biphenyl)-4,4'-diamine (NPD) and boron subphthalocyanine-chloride (SubPc) as donors with each of the acceptors aa-hh. Devices using ee and ff produced no photoresponse, although the absorption and atomic force microscopy (AFM) data suggest that ee and ff are continuous thin films. The likely reason for the poor performance is a poor match of the donor exciton energy to the LUMOs of ee and ff. Adding cyano groups shifts the LUMO levels to below that of C60, making suitable acceptors when matched with a SubPc donor. The device with a SubPc donor and cyano-aza-acene acceptor gg exhibited diode character in the dark along with photoresponse. The device current density-vs.-voltage characteristics for devices with gg are shown in FIG. 13. Compared to C60, gg exhibited significantly reduced short circuit current density (JSC), but comparable VOC: 1.78 mA/cm2 vs 4.15 mA/cm2 and 0.85 V vs 1.0 V, respectively. Additionally, the fill factor (FF) of the diaza-tetracene devices were lower compared to those made with C60: 0.40 vs 0.54, respectively, consistent with a higher resistivity for gg and hh relative to C60. While gg lacks a molecular dipole moment, the cyano groups can result in significant changes in the local electric field surrounding, the molecule leading to disorder-induced charge traps. Such enhanced resistivity is expected to lower FF, as observed. The aza substitution is not expected to give large fluctuations in the local electrical field around the molecules, and hence it is expected that the cyano-based deficiencies observed in the OPVs will be reduced or eliminated in aza-substituted materials.

What is claimed is:

1. An organic photosensitive optoelectronic device comprising at least one heterojunction at the interface of at least one donor material and at least one acceptor material, wherein the acceptor material comprises at least one aza-acene;
    wherein the aza-acene is a diaza-tetracene selected from 4,10-diphenyl-3,9-diaza-tetracene (DPDAT), 4,8,10, 14-tetraphenyl-3,9-diaza-tetracene (TPDAT), 4,10-dichloro-3,9-diaza-tetracene (DCDAT), 8,14-diphenyl-4, 10-dichloro-3,9-diaza-tetracene (DPDCDAT), 8,14-diphenyl-4,10-dicyano-3,9-diaza-tetracene (DPDCNDAT), and 4,10-dicyano-3,9-diaza-tetracene (DCNDAT).

2. The device of claim 1, wherein the diaza-tetracene is DPDCNDAT and the at least one donor material is boron subphthalocyanonine chloride(SubPc).

3. The device of claim 2 having a structure Indium Tin Oxide (ITO)/SubPc/DPDCNDAT/Bathocuproine (BCP)/Al.

* * * * *